United States Patent
Bergersen

(10) Patent No.: US 7,963,765 B2
(45) Date of Patent: Jun. 21, 2011

(54) SYSTEM OF DENTAL APPLIANCES HAVING VARIOUS SIZES AND TYPES AND A METHOD FOR TREATING MALOCCLUSIONS OF PATIENTS OF VARIOUS AGES WITHOUT ADJUSTMENTS OR APPOINTMENTS

(75) Inventor: Earl O. Bergersen, Dorado, PR (US)

(73) Assignee: Ortho-Tain, Inc, Dorado, PR (US)

( * ) Notice: Subject to any disclaimer, the term of this patent is extended or adjusted under 35 U.S.C. 154(b) by 1596 days.

(21) Appl. No.: 10/665,441

(22) Filed: Sep. 18, 2003

(65) Prior Publication Data
US 2004/0058295 A1    Mar. 25, 2004

Related U.S. Application Data

(60) Provisional application No. 60/412,511, filed on Sep. 20, 2002.

(51) Int. Cl.
*A61C 7/00* (2006.01)
(52) U.S. Cl. ............................................................. 433/6
(58) Field of Classification Search ................ 433/6, 24; 128/861
See application file for complete search history.

(56) References Cited

U.S. PATENT DOCUMENTS

| | | | | |
|---|---|---|---|---|
| 3,178,820 A | * | 4/1965 | Kesling | ............................... 433/6 |
| 3,724,075 A | | 4/1973 | Kesling | |
| 3,837,081 A | | 9/1974 | Kesling | |
| 4,073,061 A | | 2/1978 | Bergersen | ......................... 32/14 |
| 4,105,032 A | | 8/1978 | Blomstedt | |
| 4,139,944 A | * | 2/1979 | Bergersen | ......................... 433/6 |
| 4,370,129 A | | 1/1983 | Huge | |
| 4,371,336 A | | 2/1983 | Hilleman | |
| 4,396,373 A | | 8/1983 | Dellinger | |
| 4,568,280 A | | 2/1986 | Ahlin | |
| 4,591,341 A | | 5/1986 | Andrews | |
| 4,784,605 A | | 11/1988 | Bergersen | ......................... 433/6 |
| 4,799,884 A | | 1/1989 | Bergersen | ......................... 433/6 |
| 4,830,612 A | | 5/1989 | Bergersen | ......................... 433/6 |
| 4,898,535 A | | 2/1990 | Bergersen | ......................... 433/6 |
| 4,919,612 A | | 4/1990 | Bergersen | ......................... 433/6 |

(Continued)

FOREIGN PATENT DOCUMENTS
WO    PCT/US03/29662    9/2003

OTHER PUBLICATIONS
Written Opinion for PCT/US03/29662 mailed Aug. 4, 2004.
(Continued)

*Primary Examiner* — Ralph A Lewis
(74) *Attorney, Agent, or Firm* — Patents + TMS, P.C.

(57) ABSTRACT

A system of dental appliances having various sizes and types and a method for treating malocclusions of patients of various ages without adjustments or appointments are provided. The dental appliances may be sized to treat, for example, patients in age ranges of less than six years; six years to twelve years; and twelve or more years. The dental appliances may have preformed and/or customized sockets and/or slots for more than one tooth, such as incisors and/or canines and/or molars and/or premolars and/or deciduous molars and/or adult molars. The dental appliances may be one-size-fits-all type dental appliances. The dental appliances may be used to treat a malocclusion, such as, for example, an overbite, an overjet, crowding, spacing, or temporomandibular joint problems, and may be distributed in an over-the-counter manner.

45 Claims, 15 Drawing Sheets

U.S. PATENT DOCUMENTS

| | | |
|---|---|---|
| 4,983,334 A | 1/1991 | Adell |
| 4,986,751 A | 1/1991 | Bergersen |
| 5,028,231 A | 7/1991 | Hall |
| 5,037,294 A | 8/1991 | Bergersen ............ 433/6 |
| 5,037,295 A | 8/1991 | Bergersen ............ 433/6 |
| 5,042,506 A | 8/1991 | Liberati |
| D323,215 S | 1/1992 | Bergersen ............ D24/180 |
| 5,194,004 A * | 3/1993 | Bergersen ............ 433/215 |
| 5,203,695 A * | 4/1993 | Bergersen ............ 433/6 |
| 5,328,362 A | 7/1994 | Watson et al. |
| 5,334,218 A | 8/1994 | Johnson |
| 5,338,190 A | 8/1994 | Tregillis |
| 5,645,420 A | 7/1997 | Bergersen ............ 433/6 |
| 5,683,244 A | 11/1997 | Truax |
| 5,779,470 A | 7/1998 | Kussick |
| 5,814,074 A | 9/1998 | Branam |
| 5,816,799 A | 10/1998 | Parker |
| 5,876,199 A | 3/1999 | Bergersen ............ 433/6 |
| 5,882,192 A | 3/1999 | Bergersen |
| 5,911,576 A | 6/1999 | Ulrich et al. |
| 5,975,893 A | 11/1999 | Chishti et al. |
| 6,129,084 A | 10/2000 | Bergersen ............ 128/848 |
| 6,299,440 B1 | 10/2001 | Phan et al. |
| 6,454,565 B2 | 9/2002 | Phan et al. |
| 6,505,625 B1 | 1/2003 | Uenishi |
| 6,582,225 B1 * | 6/2003 | Bergersen ............ 433/2 |
| 6,626,664 B1 * | 9/2003 | Bergersen ............ 433/6 |

OTHER PUBLICATIONS

Search Report for PCT/US03/29662 mailed Dec. 24, 2003.

* cited by examiner

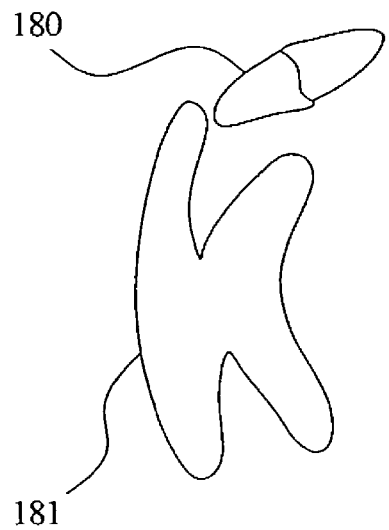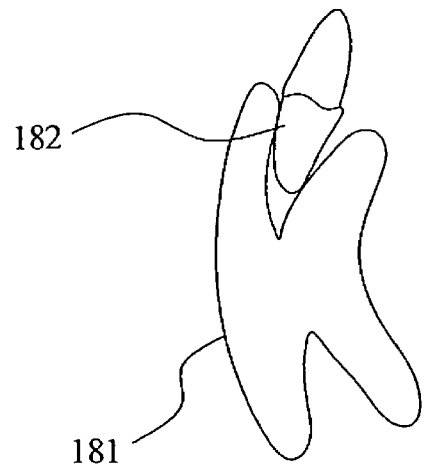
FIG. 18A   FIG. 18B
FIG. 19A   FIG. 19B   FIG. 19C
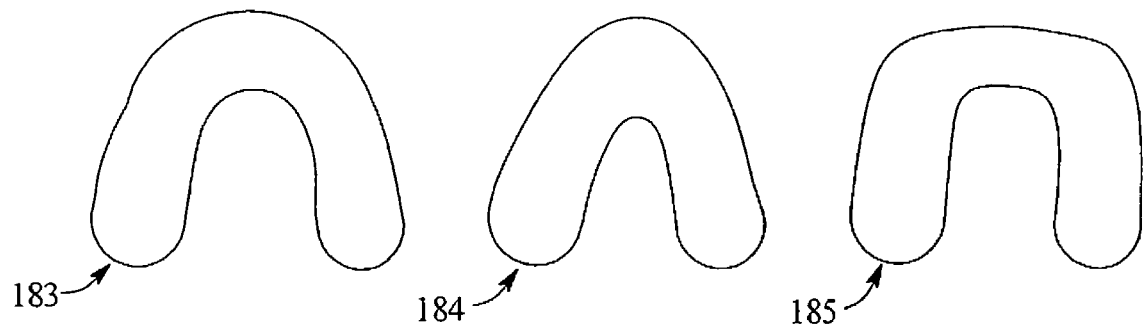

SYSTEM OF DENTAL APPLIANCES HAVING VARIOUS SIZES AND TYPES AND A METHOD FOR TREATING MALOCCLUSIONS OF PATIENTS OF VARIOUS AGES WITHOUT ADJUSTMENTS OR APPOINTMENTS

This application claims the benefit of U.S. Provisional Application Serial No. 60/412,511, filed Sep. 20, 2002.

BACKGROUND OF THE INVENTION

The present invention relates to a system of dental appliances having various sizes and types which may be used to treat a child, an adolescent and/or an adult patient to obtain a satisfactory orthodontic result without adjustments or appointments, enabling the dental appliance to be sold directly to the public over the counter. The various dental appliances may treat a malocclusion such as, for example, an overjet, an overbite, temporomandibular problems, crowding, rotations and/or spacing.

It is generally known to provide dental care to a patient. Typically, the patient visits, for example, a dentist or other type of care provider at the office of the care provider. The dentist, upon examination of the patient, may provide the patient with a dental appliance to treat the condition of the patient. For example, a patient may have an overbite which may require a dental appliance to be placed within the mouth of the patient.

Dental care subsequent to placement of the dental appliance within the mouth may require, for example, fixing bracket attachments and/or bands to most or all of the teeth. In addition, adjustable wires may be implemented, and force may be applied towards the teeth by, for example, rubber bands, springs, wires, levers, or the like, to move the teeth of the patient into a proper location. Guidance of teeth often requires one or more adjustments and/or dental office visits. As a result, the patient may be required to allot a considerable amount of time towards receiving dental care.

Various removable dental appliances have been developed in an attempt to make dental treatment simpler, less time-consuming, and/or less costly to the patient. Often these removable dental appliances correct one or two specific tooth movements or problems, but do not correct an entire dentition.

Other known dental appliances replace preformed sockets with a single groove or slot in an attempt to design a dental appliance which simplifies its effects on a dentition. However, these single-slotted dental appliances cause various problems when correcting a midline, space closure, overbite, eruption guidance, overjet, temporomandibular joint problems, rotations, crowding, etc.

For example, a single, slotted dental appliance has no interruptions in the slot to allow the dental appliance to place force in a mesio-distal direction, forward or backward, on either side of a mouth, or from left to right in the front of the mouth. As a result, a midline of the user cannot be corrected and/or spaces existing between the teeth when there is little overjet present cannot be closed. To properly correct overbite, space closure at the front of the mouth is essential; therefore, overbite cannot be adequately corrected. Correction of overjet in an absence of overbite correction causes temporomandibular joint problems which cannot be corrected when initially present. If the user wears a dental appliance which does not have sockets at a time when the teeth are erupting, proper guidance of teeth cannot be accomplished. Moreover, crowding and/or rotations may also occur and, if present, may not be properly corrected.

In addition, known dental appliances having a single groove or slot may treat patients in a first age group but may not be sized and/or designed to treat patients of a second age group.

A need, therefore, exists for a system of dental appliances having various sizes and types and a method for treating malocclusions of patients of various ages without adjustments wherein the dental appliances may treat patients of various ages efficiently to obtain a satisfactory result without any adjustments or appointments.

SUMMARY OF THE INVENTION

The present invention relates to a system of dental appliances having various sizes and types and a method for treating malocclusions of patients of various ages without adjustments or appointments. In general, patients may have different sets of teeth erupting at different developmental stages of a dentition. Accordingly, in an embodiment, a dental appliance within the system may have an area which may receive an incisor, a canine, a premolar and/or deciduous molar and/or a permanent molar which is sized specifically to correct a malocclusion of the patient, depending on the age and/or number and/or type of teeth present in that patient.

To this end, in an embodiment of the present invention, a dental appliance is provided which is worn in a mouth of a user having one or more types of teeth. The dental appliance has a generally U-shaped base having a flat occlusal surface wherein the occlusal surface contacts the teeth. The dental appliance also has a first wall extending from the flat surface wherein the first wall defines an interior surface. In addition, the dental appliance has a second wall extending from the flat surface wherein the second wall defines an exterior surface and wherein the first wall and the second wall define a width of the occlusal surface wherein the width increases from a first portion of the base which contacts a front of the mouth to a second portion which extends further rearward in the mouth.

In an embodiment, the first portion contacts an incisor type of tooth.

In an embodiment, the second portion contacts a canine type of tooth.

In an embodiment, the dental appliance has lingual tabs formed within the interior surface wherein the lingual tabs extend rearward into the mouth of the user.

In an embodiment, the base is constructed from a moisture-absorbent material.

In an embodiment, the base is constructed from a first material and a second material wherein the first material is softer than the second material.

In an embodiment, the dental appliance has suction cups formed with the base.

In another embodiment of the present invention, a dental appliance is provided which is worn in a mouth of a user having one or more types of teeth wherein one of the types of teeth is canine teeth. The dental appliance has a generally U-shaped base having an occlusal surface which contacts the teeth when the base is worn. The dental appliance also has wedges formed within the occlusal surface wherein each of the wedges form an apex which extends toward a canine tooth and contacts the canine tooth to move the canine tooth to prevent malocclusion within the mouth.

In an embodiment, the dental appliance has a second base attached to the U-shaped base wherein the second base has an occlusal surface.

In an embodiment, the dental appliance has one or more sockets wherein the sockets are shaped to receive a second type of teeth wherein the type is not canine teeth.

In an embodiment, the base is thicker in an area which contacts a first type of teeth than a second area that contacts a second type of teeth.

In an embodiment, the dental appliance has a wire embedded within the base.

In an embodiment, the base is sized to contact only one tooth.

In another embodiment of the present invention, a dental appliance is provided which is worn in a mouth of a user having teeth. The dental appliance has a generally U-shaped base. The dental appliance also has sockets within the base. In addition, the dental appliance has a suction cup extending from the base wherein the suction cup has a concave surface which contacts the mouth and adheres to the mouth to prevent movement of the base when the base is worn in the mouth.

In an embodiment, the suction cup is removably attached to the base.

In an embodiment, the sockets are preformed.

In an embodiment, the sockets are customized.

In an embodiment, the dental appliance has wedges formed on the base wherein the wedges contact the teeth of the user.

In an embodiment, the sockets are flat.

In an embodiment, the dental appliance has a liner on the base wherein the liner has a surface which contacts the mouth to prevent the base from moving within the mouth.

It is, therefore, an advantage of the present invention to provide a system of dental appliances having various sizes and types and a method for treating malocclusions of patients of various ages without adjustments.

Another advantage of the present invention is to provide a system of dental appliances having various sizes and types and a method for treating malocclusions of patients of various ages without adjustments or appointments which may align the upper canines.

A still further advantage of the present invention is to provide a system of dental appliances having various sizes and types and a method for treating malocclusions of patients of various ages without adjustments or appointments which may align the lower canines.

Yet another advantage of the present invention is to provide a system of dental appliances having various sizes and types and a method for treating malocclusions of patients of various ages without adjustments or appointments which may correct the upper midline and/or the lower midline.

Moreover, an advantage of the present invention is to provide a system of dental appliances having various sizes and types and a method for treating malocclusions of patients of various ages without adjustments or appointments which may close upper anterior spaces.

A further advantage of the present invention is to provide a system of dental appliances having various sizes and types and a method for treating malocclusions of patients of various ages without adjustments or appointments which may close lower anterior spaces.

Another advantage of the present invention is to provide a system of dental appliances having various sizes and types and a method for treating malocclusions of patients of various ages without adjustments or appointments which may rotate the upper incisors.

A still further advantage of the present invention is to provide a system of dental appliances having various sizes and types and a method for treating malocclusions of patients of various ages without adjustments or appointments which may rotate the lower incisors.

Yet another advantage of the present invention is to provide a system of dental appliances having various sizes and types and a method for treating malocclusions of patients of various ages without adjustments or appointments which may correct overbite.

Moreover, an advantage of the present invention is to provide a system of dental appliances having various sizes and types and a method for treating malocclusions of patients of various ages without adjustments or appointments which may correct overjet.

In addition, an advantage of the present invention is to provide a system of dental appliances having various sizes and types and a method for treating malocclusions of patients of various ages without adjustments or appointments which may maintain the mandible in an advanced position.

A further advantage of the present invention is to provide a system of dental appliances having various sizes and types and a method for treating malocclusions of patients of various ages without adjustments or appointments which may have less relapse due to increased mandibular forward advancement with more efficient lower jaw growth.

A further advantage of the present invention is to provide a system of dental appliances having various sizes and types and a method for treating malocclusions of patients of various ages without adjustments or appointments which may have less relapse due to decreased upper jaw growth.

Another advantage of the present invention is to provide a system of dental appliances having various sizes and types and a method for treating malocclusions of patients of various ages without adjustments or appointments which may provide efficient posterior intercuspation.

A still further advantage of the present invention is to provide a system of dental appliances having various sizes and types and a method for treating malocclusions of patients of various ages without adjustments or appointments which may provide less gingival irritation due to more customized margins specific to an age of a patient.

Yet another advantage of the present invention is to provide a system of dental appliances having various sizes and types and a method for treating malocclusions of patients of various ages without adjustments or appointments which may provide for more consistent wear due to more customized fit.

Moreover, an advantage of the present invention is to provide a system of dental appliances having various sizes and types and a method for treating malocclusions of patients of various ages without adjustments or appointments which may provide bucco-lingual and mesio-distal control of upper premolars.

Another advantage of the present invention is to provide a system of dental appliances having various sizes and types and a method for treating malocclusions of patients of various ages without adjustments or appointments which may provide bucco-lingual and mesio-distal control of lower premolars.

In addition, an advantage of the present invention is to provide a system of dental appliances having various sizes and types and a method for treating malocclusions of patients of various ages without adjustments or appointments which may provide bucco-lingual and mesio-distal control of upper molars.

A further advantage of the present invention is to provide a system of dental appliances having various sizes and types and a method for treating malocclusions of patients of various ages without adjustments or appointments which may provide bucco-lingual and mesio-distal control of lower molars.

Yet another advantage of the present invention is to provide a system of dental appliances having various sizes and types and a method for treating malocclusions of patients of various ages without adjustments or appointments which may provide an increased amount of space for crowded teeth.

Moreover, an advantage of the present invention is to provide a system of dental appliances having various sizes and types and a method for treating malocclusions of patients of various ages without adjustments or appointments which may provide cooperation with a mouth of a patient due to a customized fit.

A still further advantage of the present invention is to provide a system of dental appliances having various sizes and types and a method for treating malocclusions of patients of various ages without adjustments or appointments which may straighten teeth, reducing a need for fixed orthodontics.

A further advantage of the present invention is to provide a system of dental appliances having various sizes and types and a method for treating malocclusions of patients of various ages without adjustments or appointments which may provide a technique and method of orthodontics to distribute dental appliances directly to the public in an over-the-counter manner without a need for a professional care provider diagnosing or observing the patient.

Yet another advantage of the present invention is to provide a system of dental appliances having various sizes and types and a method for treating malocclusions of patients of various ages without adjustments or appointments which may provide orthodontic treatment without adjustments.

A further advantage of the present invention is to provide a system of dental appliances having various sizes and types and a method for treating malocclusions of patients of various ages without adjustments or appointments which may provide orthodontic treatment without appointments.

Another advantage of the present invention is to provide a system of dental appliances having various sizes and types and a method for treating malocclusions of patients of various ages without adjustments or appointments which may have higher and thicker margins than known dental appliances and may guide improperly erupting incisors, canines and premolars into a proper occlusion.

In addition, an advantage of the present invention is to provide a system of dental appliances having various sizes and types and a method for treating malocclusions of patients of various ages without adjustments or appointments which may correct crossbites of different teeth.

Yet another advantage of the present invention is to provide a system of dental appliances having various sizes and types and a method for treating malocclusions of patients of various ages without adjustments or appointments which may receive cross-bite wire within margins of the dental appliance.

A further advantage of the present invention is to provide a system of dental appliances having various sizes and types and a method for treating malocclusions of patients of various ages without adjustments or appointments which may receive reliner within sockets and/or slots of the dental appliance.

A still further advantage of the present invention is to provide a system of dental appliances having various sizes and types and a method for treating malocclusions of patients of various ages without adjustments or appointments which may have reliner held to the dental appliance as a result of a meshed and roughened surface of the dental appliance.

Another advantage of the present invention is to provide a system of dental appliances having various sizes and types and a method for treating malocclusions of patients of various ages without adjustments or appointments which may have a pointed cusp in a socket to control eruption of canine teeth.

Yet another advantage of the present invention is to provide a system of dental appliances having various sizes and types and a method for treating malocclusions of patients of various ages without adjustments or appointments which may have sharp incisal edges in sockets and/or slots to rotate incisors.

Moreover, an advantage of the present invention is to provide a system of dental appliances having various sizes and types and a method for treating malocclusions of patients of various ages without adjustments or appointments which may have sharp cusps and/or incisal edges in sockets and/or slots which may cause depressive forces against incisors and canines.

A further advantage of the present invention is to provide a system of dental appliances having various sizes and types and a method for treating malocclusions of patients of various ages without adjustments or appointments which may control different arch forms.

Another advantage of the present invention is to provide a system of dental appliances having various sizes and types and a method for treating malocclusions of patients of various ages without adjustments or appointments which may have interproximal ribs to assist in guiding teeth mesio-distally.

A still further advantage of the present invention is to provide a system of dental appliances having various sizes and types and a method for treating malocclusions of patients of various ages without adjustments or appointments which may rotate teeth by having an elongated elevation to rotate teeth with more pressure on their mesial and distal surfaces in a labial area and/or a buccal area and/or a lingual area.

Yet another advantage of the present invention is to provide a system of dental appliances having various sizes and types and a method for treating malocclusions of patients of various ages without adjustments or appointments which may have a roughened area across the incisal area of the dental appliance on the labial surface to better retain whitening strips.

A still further advantage of the present invention is to provide a system of dental appliances having various sizes and types and a method for treating malocclusions of patients of various ages without adjustments or appointments which may have a roughened area across an incisal area of the dental appliance on a labial surface to better retain a whitening gel.

A further advantage of the present invention is to provide a system of dental appliances having various sizes and types and a method for treating malocclusions of patients of various ages without adjustments or appointments which may absorb fluoride liquid or gel prevent decay of the teeth.

Moreover, an advantage of the present invention is to provide a system of dental appliances having various sizes and types and a method for treating malocclusions of patients of various ages without adjustments or appointments which may prevent the development of an overbite and/or gummy smile.

An additional advantage of the present invention is to provide a system of dental appliances having various sizes and types and a method for treating malocclusions of patients of various ages without adjustments or appointments which may contact and treat a front portion of a mouth of a patient.

Yet another advantage of the present invention is to provide a system of dental appliances having various sizes and types and a method for treating malocclusions of patients of various ages without adjustments or appointments which may have suction cups on the interior surface of the dental appliance, in the sockets of the dental appliance to move teeth bodily and/or rotate teeth.

A further advantage of the present invention is to provide a system of dental appliances having various sizes and types and a method for treating malocclusions of patients of various ages without adjustments or appointments which may have an elastomeric material and/or string glued or otherwise attached to the interior of the dental appliance wherein the dental appliance may rotate, torque and/or depress teeth or a single tooth.

Another advantage of the present invention is to provide a system of dental appliances having various sizes and types and a method for treating malocclusions of patients of various ages without adjustments or appointments which may be designed by a computer and molded from a computer program by a vacuum or pressure type device or by stereolithography.

A still further advantage of the present invention is to provide a system of dental appliances having various sizes and types and a method for treating malocclusions of patients of various ages without adjustments or appointments which may straighten only the teeth of a single arch.

Moreover, an advantage of the present invention is to provide a system of dental appliances having various sizes and types and a method for treating malocclusions of patients of various ages without adjustments or appointments which may be distributed over-the-counter.

Yet another advantage of the present invention is to provide a system of dental appliances having various sizes and types and a method for treating malocclusions of patients of various ages without adjustments or appointments which may correct crowding or spacing of a dentition.

An additional advantage of the present invention is to provide a system of dental appliances having various sizes and types and a method for treating malocclusions of patients of various ages without adjustments or appointments which may fluoridate or whiten the teeth without applying material to the soft tissues of the labial surface of the cheeks of the patient while maintaining contact between the teeth and a gel.

A further advantage of the present invention is to provide a system of dental appliances having various sizes and types and a method for treating malocclusions of patients of various ages without adjustments or appointments which may provide an increased vertical distance separating the front teeth as compared to the back teeth to correct temporomandibular (TMJ) joint problems due to the advancement of the lower jaw in an end-to-end relation.

A still further advantage of the present invention is to provide a system of dental appliances having various sizes and types and a method for treating malocclusions of patients of various ages without adjustments or appointments which may correct overjet and mandibular (lower jaw) retrusion.

Yet another advantage of the present invention is to provide a system of dental appliances having various sizes and types and a method for treating malocclusions of patients of various ages without adjustments or appointments which may be constructed of a stiffer material in a first area to restrict tooth movement and may be constructed of a softer material in a second area to rotate and move teeth without causing pain to the patient.

Another advantage of the present invention is to provide a system of dental appliances having various sizes and types and a method for treating malocclusions of patients of various ages without adjustments or appointments which may have a wire incorporated into the dental appliance which may expand or constrict an arch.

A further advantage of the present invention is to provide a system of dental appliances having various sizes and types and a method for treating malocclusions of patients of various ages without adjustments or appointments which may utilize a double wire which may place a squeezing force on the labial surface and lingual surface of the anterior teeth to align the anterior teeth.

An additional advantage of the present invention is to provide a system of dental appliances having various sizes and types and a method for treating malocclusions of patients of various ages without adjustments or appointments which may utilize a measuring device to measure one or more teeth to obtain a correct size for the dental appliance.

Yet another advantage of the present invention is to provide a system of dental appliances having various sizes and types and a method for treating malocclusions of patients of various ages without adjustments or appointments which may have entirely preformed tooth sockets and/or preformed slots, or a combination of tooth sockets and/or preformed slots, to be in coordination to one another to straighten and align the teeth.

A further advantage of the present invention is to provide a system of dental appliances having various sizes and types and a method for treating malocclusions of patients of various ages without adjustments or appointments which may have entirely custom-made sockets and/or slots designed from models from the patient or obtained from a digitized model from a computer and stereolithography.

A still further advantage of the present invention is to provide a system of dental appliances having various sizes and types and a method for treating malocclusions of patients of various ages without adjustments or appointments which may provide a greater space closure than known dental appliances.

Additional features and advantages of the present invention are described in, and will be apparent from, the detailed description of the presently preferred embodiments and from the drawings.

BRIEF DESCRIPTION OF THE DRAWINGS

FIG. 18A illustrates a cross-sectional view of a canine of a patient in relation to a dental appliance in an embodiment of the present invention.

FIG. 18B illustrates a cross-sectional view of the canine of the patient in relation to the dental appliance of FIG. 18A.

FIG. 19A illustrates a top plan view of a dental appliance in an embodiment of the present invention.

FIG. 19B illustrates a top plan view of a dental appliance in an embodiment of the present invention.

FIG. 19C illustrates a top plan view of a dental appliance in an embodiment of the present invention.

DETAILED DESCRIPTION OF THE PRESENTLY PREFERRED EMBODIMENTS

Figure 1:
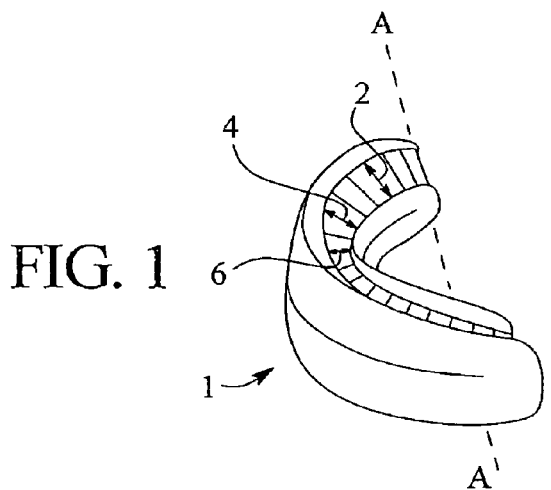
FIG. 1 illustrates a perspective view of a dental appliance in an embodiment of the present invention.

The present invention relates to a system of dental appliances having various sizes and types and a method for treating malocclusions of patients of various ages without adjustments or appointments. In an embodiment, a dental appliance may have, for example, four areas. A first, or incisal area, may have a narrowed slot labio-lingually. The incisal area may have different lengths mesio-distally to accommodate one or more dentition sizes. A second, or canine area of the dental appliance may be located at a distal end of the incisal area. The canine area may be wedge-shaped to imitate an angular double incisal edge of the canine. A distal incline of the incisal edge is essential to "squeeze" together the incisors of a patient. The squeezing may force spaces at a front of the mouth to close. The incisors may then become properly centered in the mouth when the canine wedge is properly positioned on both sides of the upper incisors and the lower incisors.

A third area of the dental appliance may have a premolar or deciduous molar area. The third area may be shaped bucco-lingually to accommodate patients up to eleven years of age having deciduous molars. In an embodiment, the third area may be shaped bucco-lingually to accommodate patients of eleven years or more having premolars that are narrower bucco-lingually.

The dental appliance may also have a fourth or adult molar area which may be wider bucco-lingually than the premolar area. The greater width may force the premolars to be properly positioned bucco-lingually and mesio-distally. The four areas of the dental appliance, particularly the incisor and canine areas, may have various sizes. As a result, the dental appliance may treat patients having various sized teeth.

Table I (below) provides examples of dimensions of dental appliances in the system of dental appliances. The table, however, should not be understood to limit the size of the dental appliance to these specific dimensional measures.

TABLE I

TYPICAL SIZE FROM A FIRST DISTAL SURFACE OF
THE UPPER, PERMANENT TOOTH ON A FIRST SIDE TO
A SECOND DISTAL SURFACE ON A SECOND SIDE ALONG
A CONTACT AREA OF THE TEETH:

|  | Child 4–6 yrs* Upper Four Incisors | Adolescent 7–12 yrs* Upper Four Incisors | Adult 12 yrs. & up** Upper Six Anteriors |
|---|---|---|---|
| Small | 28.4 mm | 28.4 mm | 44.0 mm |
| Medium | 32.0 mm | 32.0 mm | 48.5 mm |
| Large | 35.5 mm | 35.5 mm | 53.0 mm |
| Extra Large | 39.1 mm | 39.1 mm | 57.5 mm |

*Patients having only 4 upper incisors.
**Patients having 4 upper incisors and 2 upper canines.

In another embodiment of the present invention, the dental appliance may have a single slot with one or more upper preformed sockets and/or lower preformed sockets, or outward projections, positioned interproximally to guide teeth. The sockets may be incisor sockets, canine sockets, deciduous molar or premolar sockets, or permanent molar sockets or any combination of these sockets. Canine sockets and/or lower incisor sockets may align anterior teeth which may be essential considering that crowding most often occurs at the front of the mouth as well as in the lower arch.

Figure 4:
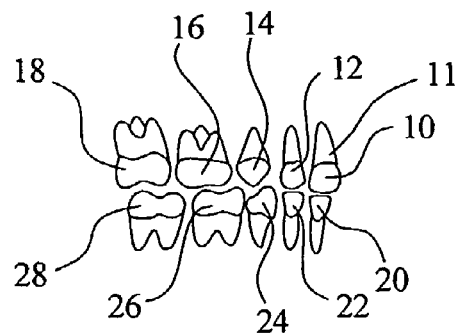
FIG. 4 illustrates a side view of upper teeth and lower teeth of an individual.

Referring now to the drawings, wherein like numerals refer to like parts, FIG. 1 illustrates a dental appliance 1 which may be worn by a patient under six years of age. The dental appliance 1 may have an area 4 which may be narrower in width than demonstrated in known dental appliances. The dental appliance 1 may accommodate an upper deciduous canine 14, illustrated in FIG. 4. The dental appliance 1 may also accommodate a lower deciduous canine 24. The area 4 may be narrower labio-lingually than a deciduous molar area 2. Moreover, the dental appliance 1 may have an area 6 for receiving upper deciduous incisors. The area 6 may be narrower labio-lingually than the area 4 or the area 2.

The dental appliance 1 may be wider bucco-lingually to accommodate deciduous molars 16, 18, 26 or 28, as opposed to narrower premolars 36, 38, 50 or 52. An area (not shown) for receiving lower deciduous incisors 20, 22 of the patient may be narrower labio-lingually than an area (not shown) for receiving a lower deciduous canine 24. In addition, the area for receiving the lower deciduous canine 24 may be narrower than an area (not shown) for receiving the lower first deciduous molars 26 and the lower second deciduous molars 28.

Figure 2:
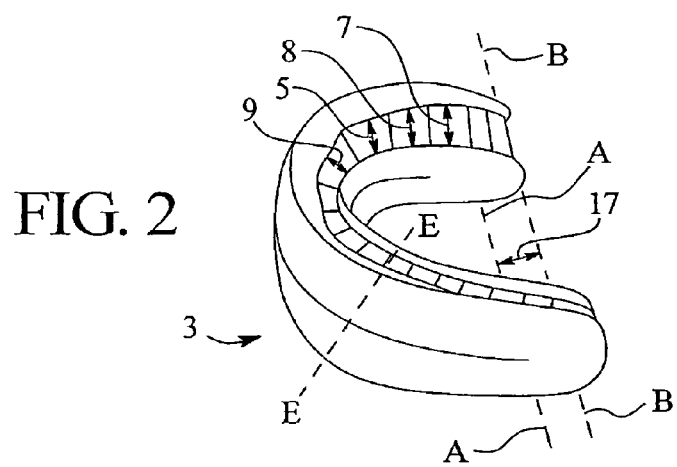
FIG. 2 illustrates a perspective view of a dental appliance in an embodiment of the present invention.
Figure 5:
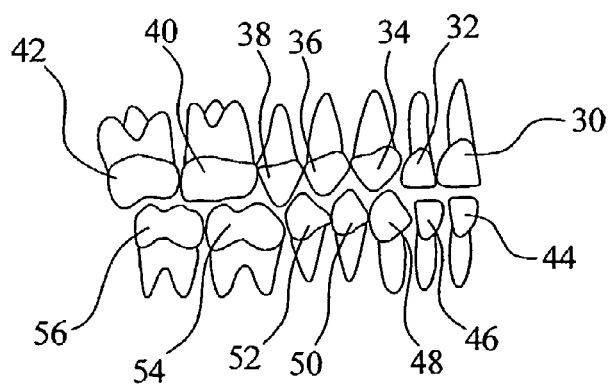
FIG. 5 illustrates a side view of upper teeth and lower teeth of an individual.

FIG. 2 illustrates a dental appliance 3 which may be worn by a patient between six to twelve years of age. The dental appliance 3 may accommodate first permanent molars 40, 54 as illustrated in FIG. 5. The dental appliance 3 may also accommodate first deciduous molars 16, 26 and/or second deciduous molars 18, 28; and/or first premolars 36, 50 or second premolars 38, 52; and/or the permanent canines 34, 48 or deciduous canines 14, 24. The dental appliance 3 may have a greater length than the dental appliance 1, as illustrated by a space 17 between lines A-A and B-B. It should be understood that the line A-A in FIG. 2 is identical to the line A-A in FIG. 1 which indicates a length of the dental appliance 1. Because first permanent molars generally erupt in the patient at about six years of age, the greater length of the dental appliance 3 may enable the dental appliance 3 to accommodate the first permanent molars 40, 54.

The dental appliance 3 may have an area 7 for receiving the upper first permanent molar 40 and the lower first permanent molar 54. The area 7 may have a greater width than an area (not shown) for receiving lower second deciduous molars 28 or a second premolar 52. The area 7 may have a greater width bucco-lingually than an area 8 for receiving a second deciduous molar 18 or a second premolar 38. The dental appliance 3 may have an area 5 for receiving the first deciduous molars 16, 26 and the first premolars 36, 50. The area 5 may have a width which may be less than the width for the area 7. The dental appliance 3 may have an area 9 which may receive the deciduous canines 14, 24 and the permanent canines 34, 48 and the permanent incisors 30, 32, 44, 46. The area 9 may have a width that is less than a width for the area 5.

Figure 3:
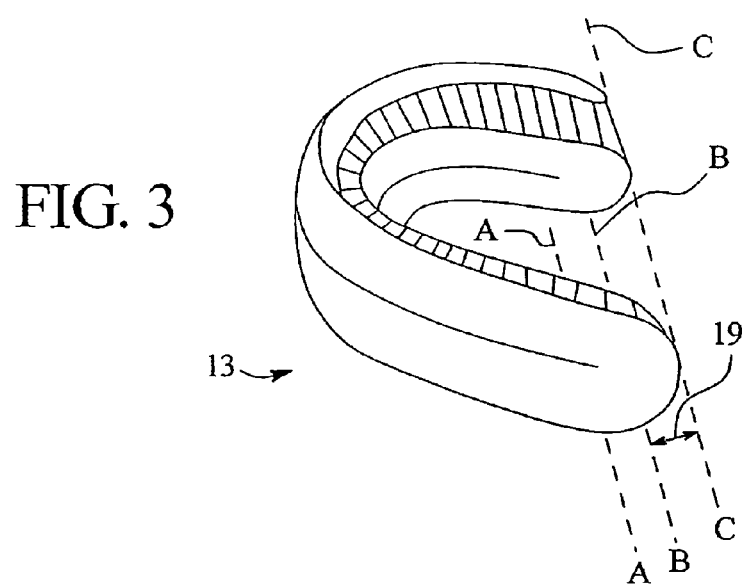
FIG. 3 illustrates a perspective view of a dental appliance in an embodiment of the present invention.

FIG. 3 illustrates a dental appliance 13 which may be worn by a patient that is twelve years of age and older.

The dental appliance 13 may have a narrower slot 15 in a bucco-lingual and mesio-distal direction. The slot 15 may receive the second premolars 38, 52. The dental appliance 13 may have a greater length than the dental appliance 3, as illustrated by a space 19 between lines B-B and C-C. It should be understood that the line B-B in FIG. 3 is identical to the line B-B in FIG. 2 which indicates a length of the dental appliance 3. It should be further understood that the line A-A in FIG. 3 is identical to the line A-A in FIG. 1. The greater length of the dental appliance 13 may enable the dental appliance 13 to treat the second permanent molars 42, 56.

Figure 6:
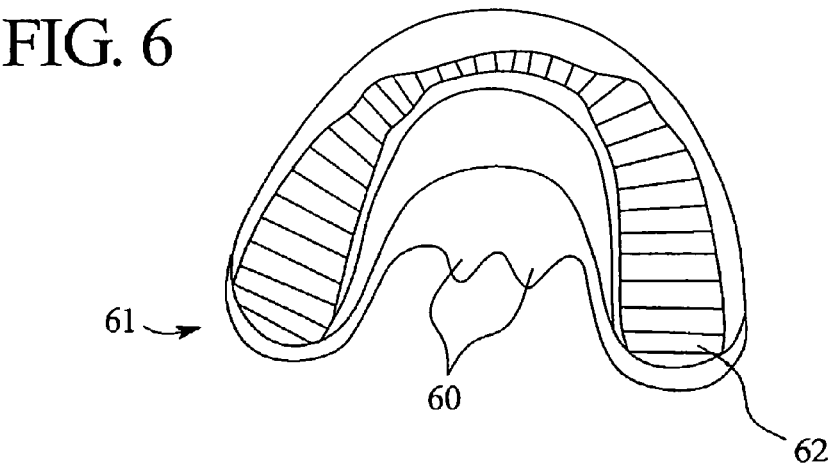
FIG. 6 illustrates a top perspective view of a dental appliance in an embodiment of the present invention.

FIG. 6 illustrates a dental appliance 61 having a slot 62 which may be specifically sized for the mouth of the patient. The dental appliance 61 may have lingual tabs 60 to maintain an advanced position of the mandible of the patient. The lingual tabs 60 may assist in antero-posterior jaw alignment and overjet correction.

Figure 7:
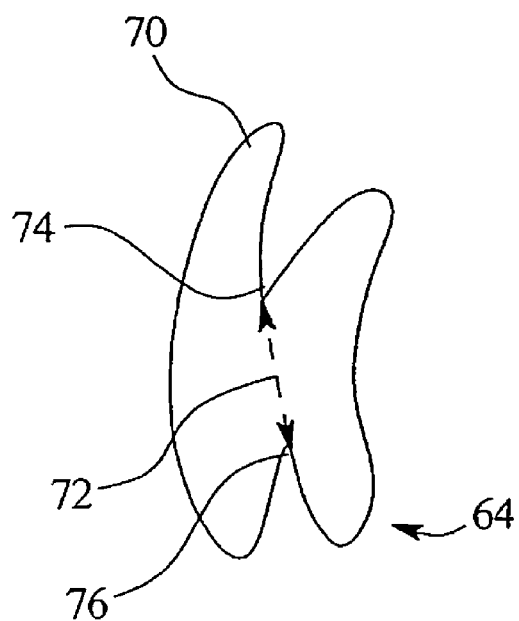
FIG. 7 illustrates a cross-sectional view of a front portion of the dental appliance of FIG. 6.

FIG. 7 illustrates a cross-sectional view of a front portion 64 of the dental appliance 61. The dental appliance 61 may have an extended upper labial margin 70 which may proceed above gingival margins of upper anterior teeth 11, illustrated in FIG. 4.

In an embodiment, an incisal slot area 74 may be shaped wherein the incisal slot area 74 is narrow. The incisal slot and/or socket area 74 may be pre-formed or customized and may consist of individualized sockets for one tooth at a time, or a slot for more than one tooth. A lower incisal slot area 76 may be shaped narrowly. In an embodiment, the dental appliance 61 may have preformed sockets (not shown) for receiving the upper incisors 30, 32 and/or receiving the lower incisors 44, 46. In general, a tooth having a thin incisal edge does not fit loosely into an incisal portion of a socket and/or slot for more than one tooth. Therefore, in the present invention, each preformed socket may have a narrow incisal edge to aid in the correction of the overbite and to increase the rotations of the incisors. In an embodiment, a socket and/or slot area (not shown) for receiving canines may be narrowly shaped than demonstrated in known dental appliances. The socket and/or slot area for receiving canines may be pre-formed or customized.

Figure 8:
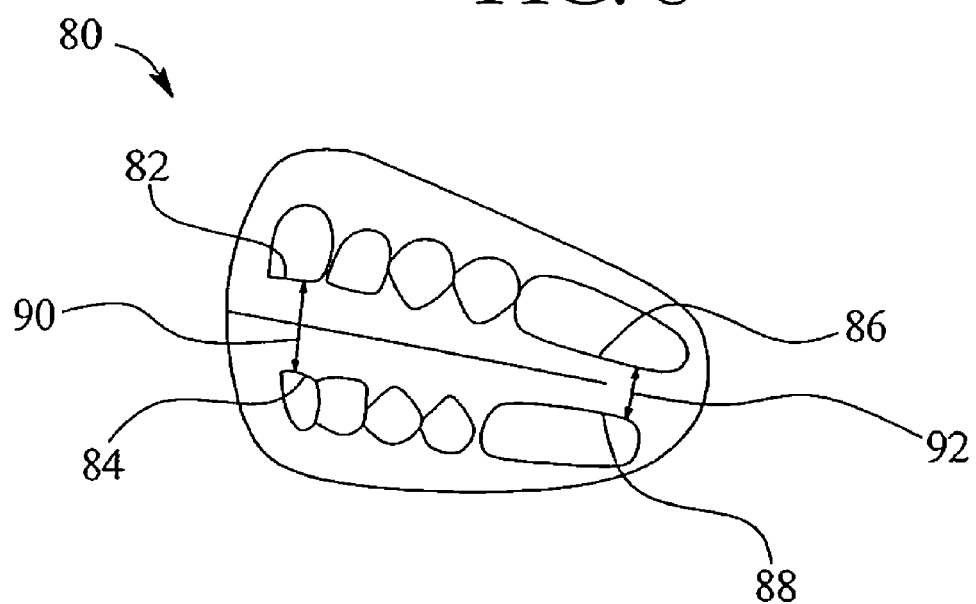
FIG. 8 illustrates a cross-sectional view of a dental appliance in an embodiment of the present invention.
Figure 9A:
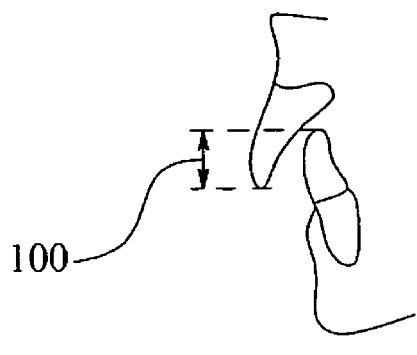
FIG. 9A illustrates a side view of an incisal relation of an individual.

In another embodiment, as illustrated in FIG. 8, a dental appliance 80 may have an isthmus 90 between incisal edges 82, 84. The dental appliance 80 may also have an isthmus 92 between occlusal surfaces 86, 88 of the upper and lower teeth. The isthmus 90 and/or the isthmus 92, as well as the dental appliance 80, may be constructed from, for example, plastic, rubber, or the like. An increase in a height of the isthmus 90 and/or a decrease in a height of the isthmus 92 may enable the dental appliance 80 to correct an overbite 100, such as that illustrated in FIG. 9A.

Figure 9B:
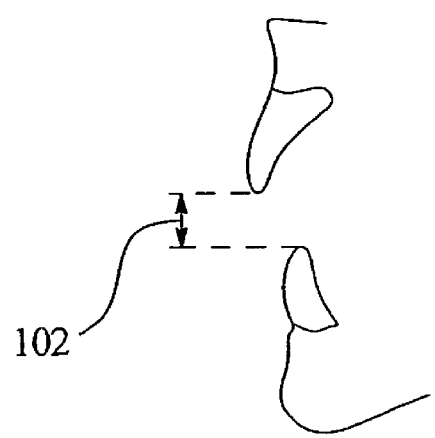
FIG. 9B illustrates a side view of an incisal relation of an individual.
Figure 10:
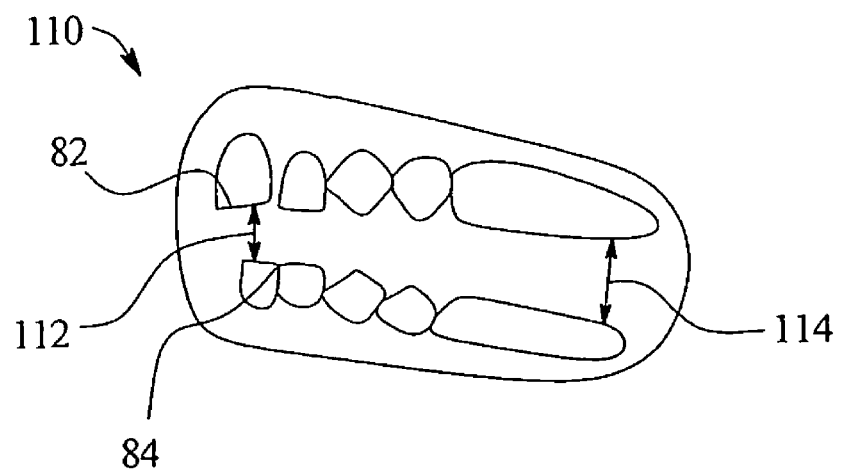
FIG. 10 illustrates a cross-sectional view of a dental appliance in an embodiment of the present invention.

In an embodiment, as illustrated in FIG. 10, a dental appliance 110 may have an isthmus 112 and an isthmus 114. The isthmus 114 may have a height which may be greater than a height of the isthmus 112 which may enable an open bite to be corrected 102. A vertical slit 72, such as that illustrated in FIG. 7, in the anterior segment (not shown) from the upper incisal edges 74 vertically to the incisal edges 76 of the lower incisors also may enable an open bite 102 to be corrected. As a result, the dental appliance 110 may treat a patient with an open bite 102, as illustrated in FIG. 9B.

Figure 11:
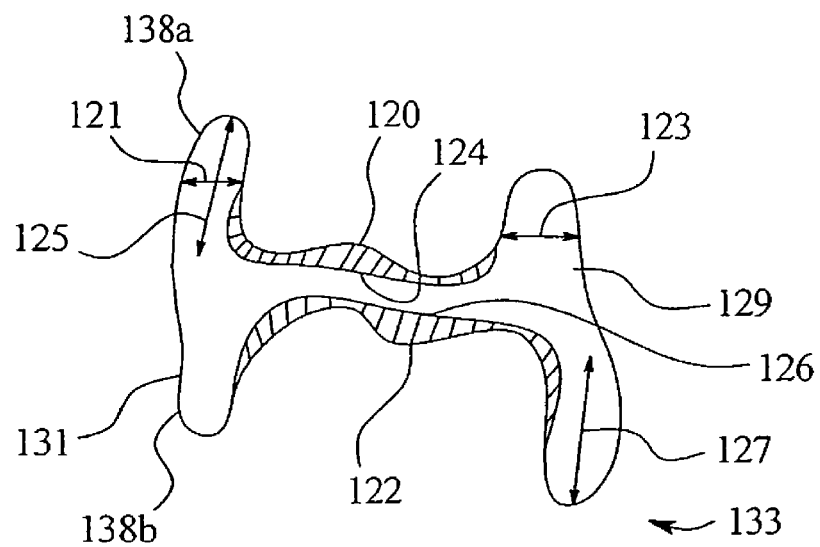
FIG. 11 illustrates a cross-sectional view of an isthmus of a dental appliance in an embodiment of the present invention.

Often, when a tooth fits loosely in a socket, proper rotations are not possible. However, in an embodiment, the dental appliance of the present invention may adjust preformed and/or customized sockets and/or slots to assist in leveling an occlusion or tooth. For example, FIG. 11 illustrates a cross-section of an isthmus 131 of a dental appliance 133. The isthmus 131 may receive the adult molar 40, 42, 54, 56, the deciduous molar 16, 18, 26, 28, and/or the premolar 36, 38, 50, 52. The isthmus 131 may have occlusal surfaces 120, 122 which may be flattened in the upper 124 and in the lower 126 to receive teeth having anatomical variations in an occlusal surface. The teeth of the patient may then fit properly in a socket designed for a specific tooth and/or group of teeth.

In general, a preformed socket for receiving a molar is designed to fit the average anatomy of an occlusal surface which has grooves 120, 122 and/or depressions of a typical occlusal surface of a molar and/or a premolar. As a result, an a typically shaped molar and/or a premolar having a flat occlusal surface may not properly fit into the preformed socket due to interferences caused by elevated grooves 120, 122 in the dental appliance socket. The back teeth may not erupt completely and/or may not allow the bite to open to properly open the bite. As a result, the overbite may not be corrected.

Figure 12:
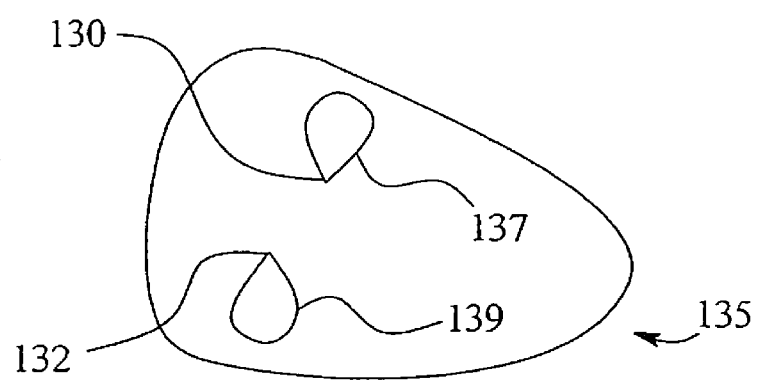
FIG. 12 illustrates a cross-sectional view of a dental appliance in an embodiment of the present invention.

FIG. 12 illustrates a cross-sectional view of a dental appliance 135 which may have sockets 137, 139 for receiving canines of the patient. The sockets 137, 139 may have points 130, 132 which may be sharper than socket points demonstrated in known dental appliances. The sockets 137, 139 may be shaped wherein any canine may fit into the sockets 137, 139 regardless of anatomical variations. As a result, the dental appliance 135 may provide leveling of an occlusion of the patient and/or intercuspation of the teeth in a canine area of the mouth. The dental appliance 135 may also assist in closure of spacing at a front of the mouth.

Figure 13:
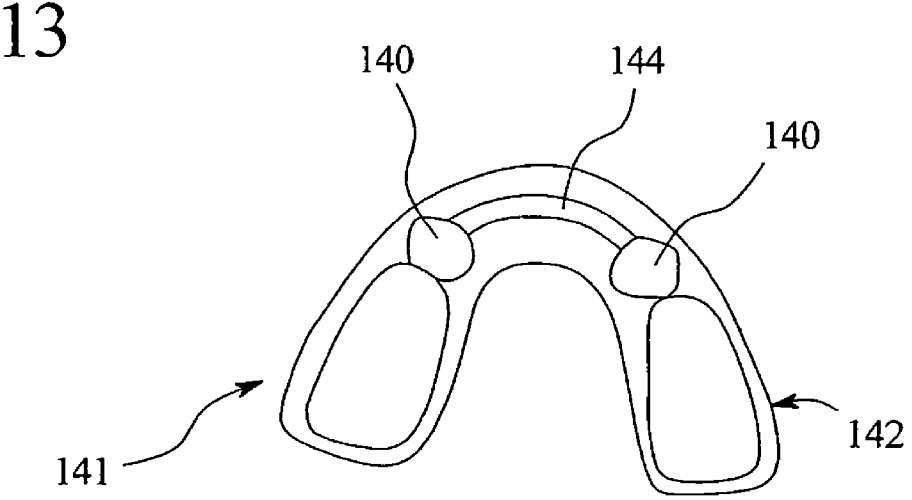
FIG. 13 illustrates a top plan view of a dental appliance in an embodiment of the present invention.
Figure 14:
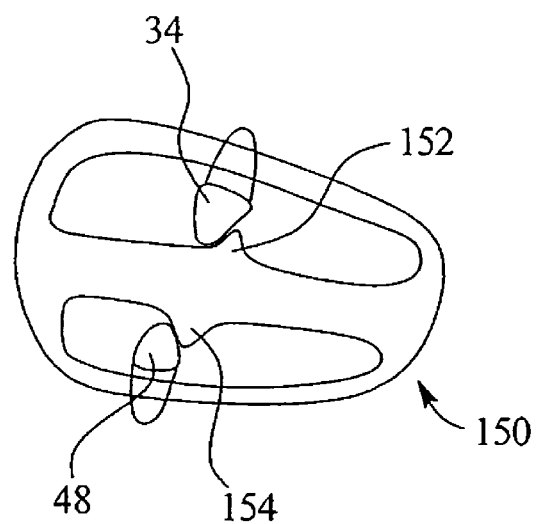
FIG. 14 illustrates a cross-sectional view of a dental appliance in an embodiment of the present invention.
Figure 15:
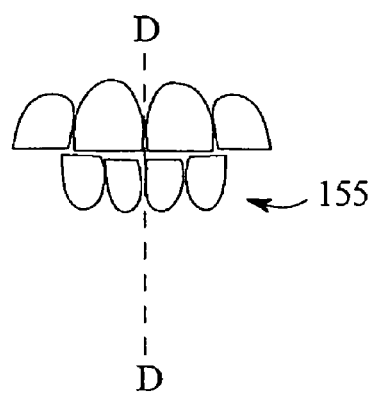
FIG. 15 illustrates a front plan view of front teeth of an individual.

In an embodiment, as illustrated in FIG. 13, a dental appliance 141 may have a slot 144 for the incisors. A single socket 140 may be provided for a canine and/or for any other teeth in both an upper arch and/or a lower arch (not shown). In another embodiment, as illustrated in FIG. 14, a dental appliance 150 may have wedges 152, 154 which may place a mesially-directed force, or a forward directed force, against the canine 34, 48. The wedges 152, 154 may assist in closing incisal spaces. The wedges 152, 154 may also assist in correcting a midline relation 155, as illustrated in FIG. 15, between the upper deciduous and/or permanent incisors 10, 30 and/or the lower incisors 20, 44 in a center of the mouth, indicated by line D-D.

Figure 16:
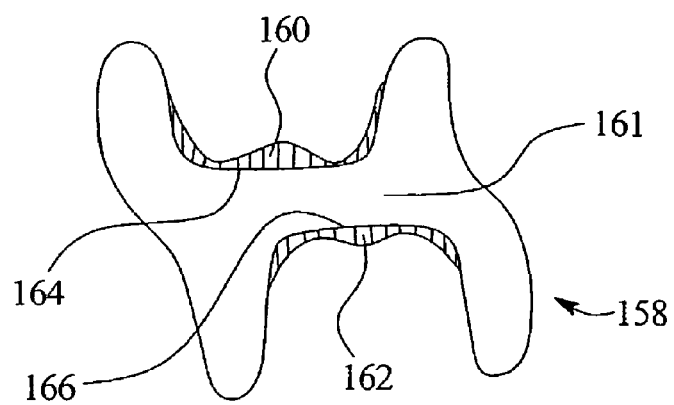
FIG. 16 illustrates a cross-sectional view of an isthmus of a dental appliance in an embodiment of the present invention.

FIG. 16 illustrates a cross-section of an isthmus 161 of a dental appliance 158 which may be a one-size-fits-all prefabricated dental appliance 158 or a full-socketed or a partial socketed/partial slotted preformed dental appliance 158. To improve the retainability of the dental appliance 158, a liner 160, 162 may be incorporated within the socket/slot area 164, 166. The liner 160, 162 may be placed inside preformed and/or customized sockets 164, 166 or slots in a region of the dental appliance 158 which may reduce or stop tooth movement when contacting teeth and may assist in retaining the dental appliance 158 within the mouth when the dental appliance 158 is worn, as well as retention of the teeth in the socket/slot area 164, 166.

The liner 160, 162 may increase an ability of the dental appliance 158 to stay in the mouth, particularly while sleeping. Moreover, the liner 160, 162 may enable the dental appliance 158 to remain in closer contact with teeth in other areas of the mouth which may require movement, rotations, or straightening. The liner 160, 162 may be constructed from, for example, hard or soft resilient plastic, rubber, a self-cure acrylic, a silicone or PVC like denture lining material, or other like material that may be placed in individual sockets or slots in certain specific areas of the dental appliance 158. The individual sockets/slot area 164, 166 may be provided on their interior with any method of roughening of their interior surface which may increase the retainability of the reline material such as undercuts. A roughened or mesh design or the like (not shown) may increase the retention of the reline material to the material of the dental appliance 158. When the teeth requiring straightening have been straightened, the liner 160, 162 may then be placed in areas of the dental appliance 158 contacting the straightened teeth to maintain a position of the straightened teeth.

Referring again to FIG. 11, the dental appliance 133 may have a buccal margin 138a, 138b which may have an extended height 125 and an extended width 121. The dental appliance 133 may also have a lingual margin 129 in an area distal to the lateral incisors and beyond an area of the gingival margins of the teeth. The lingual margin 129 may have an extended height 127 and an extended width 123. The increase in height and width of the buccal margin 138a, 138b and the lingual margin 129 may improve tooth movement. In particular, tooth movement may improve in the molar area when the dental appliance 133 is worn, either in a preformed one-size-fits-all single slotted dental appliance, a fully preformed and/or customized socketed dental appliance or a partial slotted/partial socketed preformed and/or customized dental appliance.

Moreover, the dental appliance 133 may improve eruption and/or movement of teeth displaced to the buccal or lingual.

Figure 17:
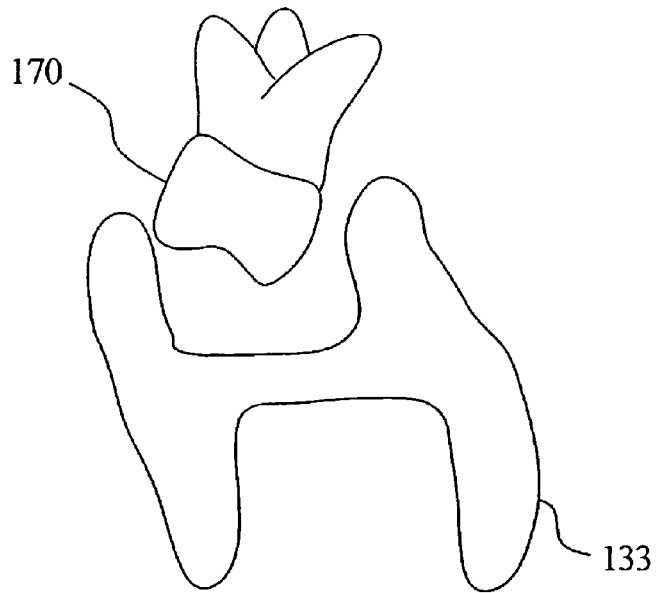
FIG. 17 illustrates a cross-sectional view of a tooth of a patient in relation to a dental appliance in an embodiment of the present invention.
Figure 20:
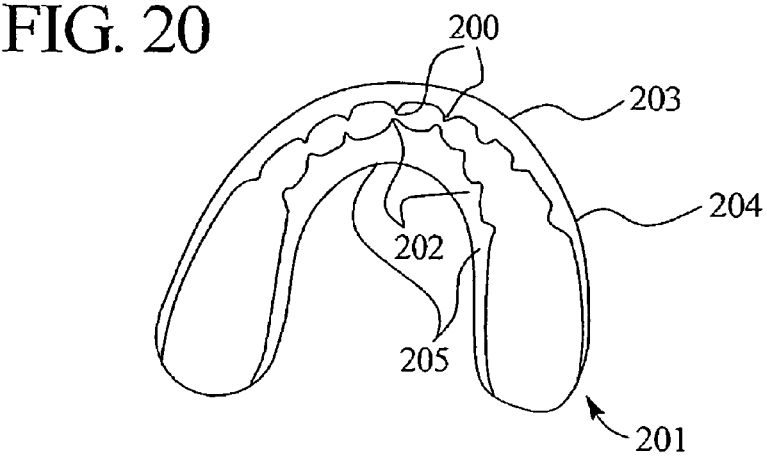
FIG. 20 illustrates a top plan view of a dental appliance in an embodiment of the present invention.

FIG. 17 illustrates a relation between a tooth 170 and the dental appliance 133. The increase in height and width of the buccal margin 138a, 138b and the lingual margin 129 may assist the dental appliance 133 in engaging incoming cusps of the tooth 170 or a displaced tooth 170 as the tooth 170 erupts or is displaced toward a buccal direction or a labial direction or to a lingual direction. The dental appliance 133 may then guide and/or move the tooth 170 into a proper position within an arch.

Figure 32:
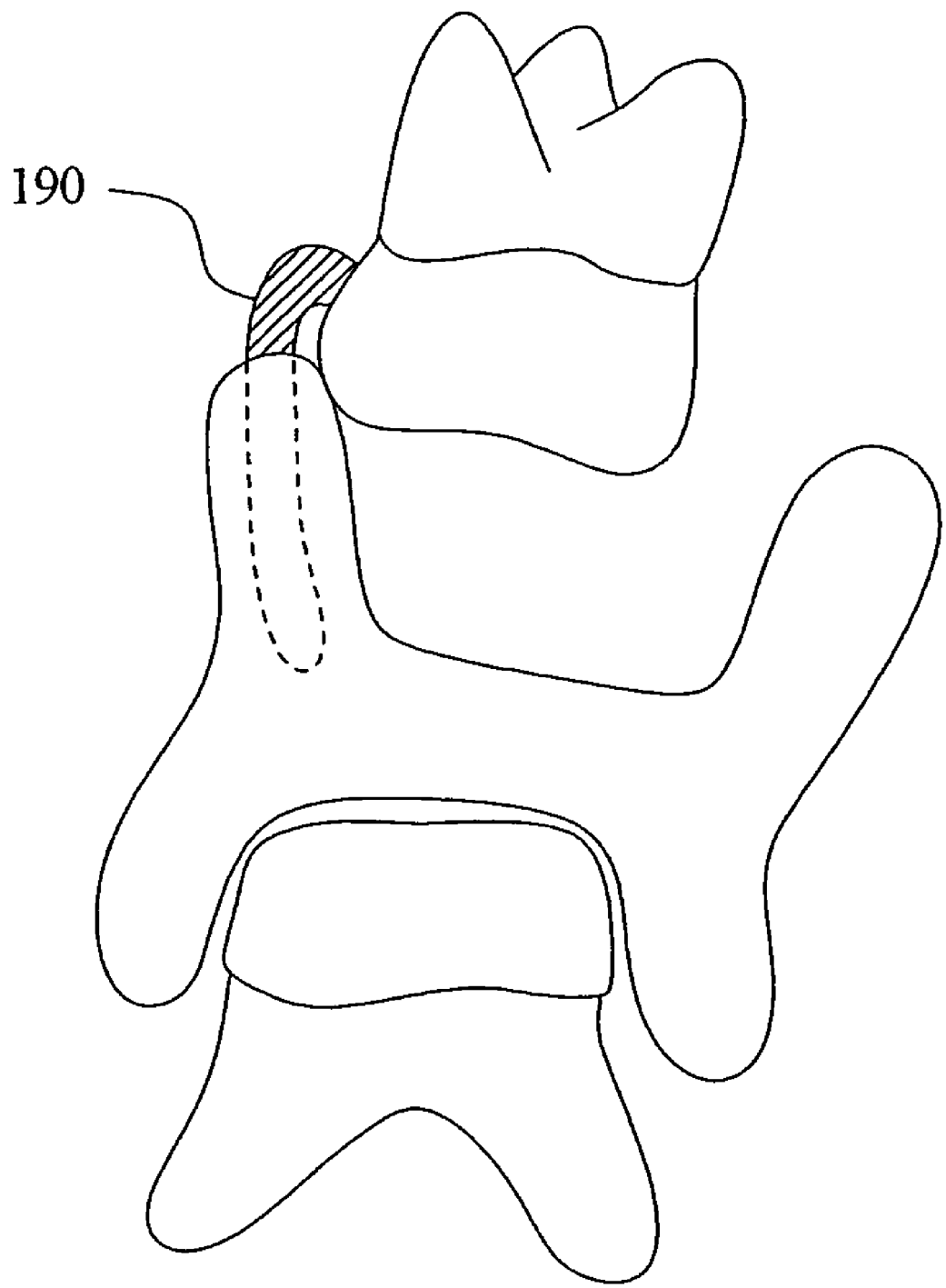
FIG. 32 illustrates a cross-sectional view of a molar of a patient in relation to a dental appliance in an embodiment of the present invention.

FIGS. 18A and 18B illustrate an example of a labially erupting and/or displaced upper canine 180 which may be guided and/or moved lingually into a proper position by the dental appliance 181. FIG. 32 illustrates a cross-bite wire insert 190 which may be implemented within the dental appliance 133 to aid in crossbite corrections. The wire insert 190 may be easily implemented within the dental appliance 133 due to the enlarged buccal margins 138a, 138b and lingual margins 129.

FIGS. 19A, 19B and 19C illustrate dental appliances 183, 184 and 185, respectively, having different shapes. Specifically, the dental appliance 183 may have a curved arch shape. The dental appliance 184 may have a tapered arch shape. The dental appliance 185 may have a square type arch shape. Dental appliances 183, 184 and 185 may have any variations of severity of such arch shapes, as well as different sizes of arches.

In an embodiment, guiding ribs or spikes 200, 202 may be provided on a dental appliance 201. The guiding ribs 200, 202 may contact a mesial interproximal area and/or distal interproximal area of the teeth. The guiding ribs 200 may be located on a labial side 203 or buccal side 204 of the dental appliance 201. The guiding ribs 202 may also be located on a lingual side 205 of the dental appliance 201.

Figure 21:
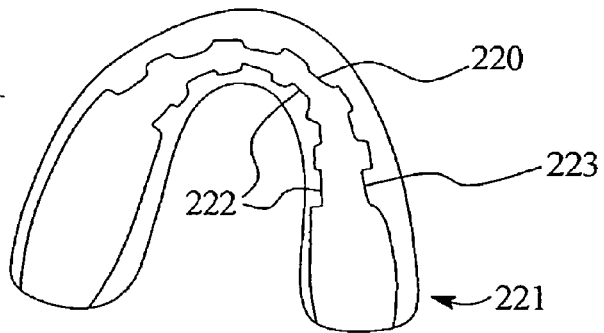
FIG. 21 illustrates a top plan view of a dental appliance in an embodiment of the present invention.

FIG. 21 illustrates a dental appliance 221 which may have an elongated, extruded area 220 which may contact a mesial surface and/or distal surface of the teeth. The elongated, extruded area 220 may be located on a labial side 220 and/or a buccal side 223 and/or a lingual side 222. The extruded area 220 may put pressure on the teeth to rotate the teeth.

Figure 22:
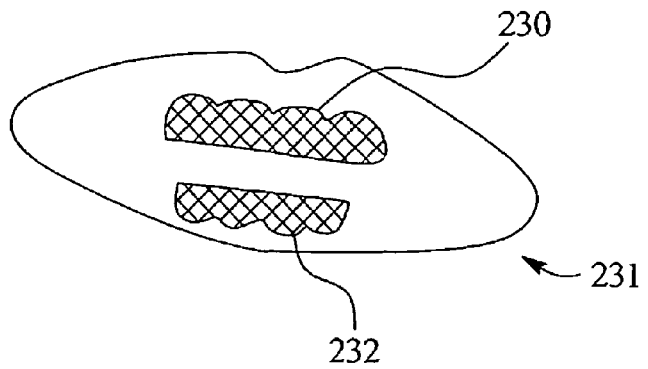
FIG. 22 illustrates a front plan view of a dental appliance in an embodiment of the present invention.

In an embodiment, illustrated in FIG. 22, a dental appliance 231 may have a roughened area 230 on a labial side of the dental appliance 231. Specifically, the roughened area 230 may be located adjacent to an upper incisor and/or canine and/or any upper tooth. A roughened area 232 may be provided on the dental appliance 231 and located adjacent a lower incisor and/or any other lower tooth. The roughened areas 230, 232 may retain whitening strips (not shown) and/or whitening gel (not shown).

In an embodiment, a dental appliance (not shown) may be constructed from, for example, a moisture absorbent plastic or other material. The dental appliance may absorb a fluoride liquid and/or gel within an interior of the dental appliance. The fluoride may then leach out of the dental appliance onto the teeth of the patient when the dental appliance is worn by the patient and may provide preventive protection against tooth decay.

Figure 23A:
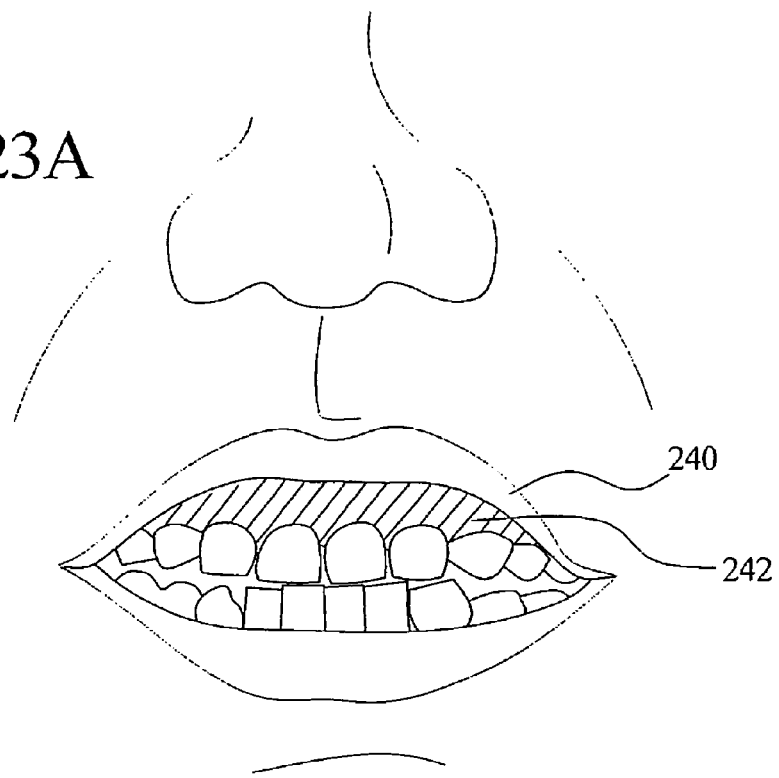
FIG. 23A illustrates a front plan view of a mouth of a patient.
Figure 23B:
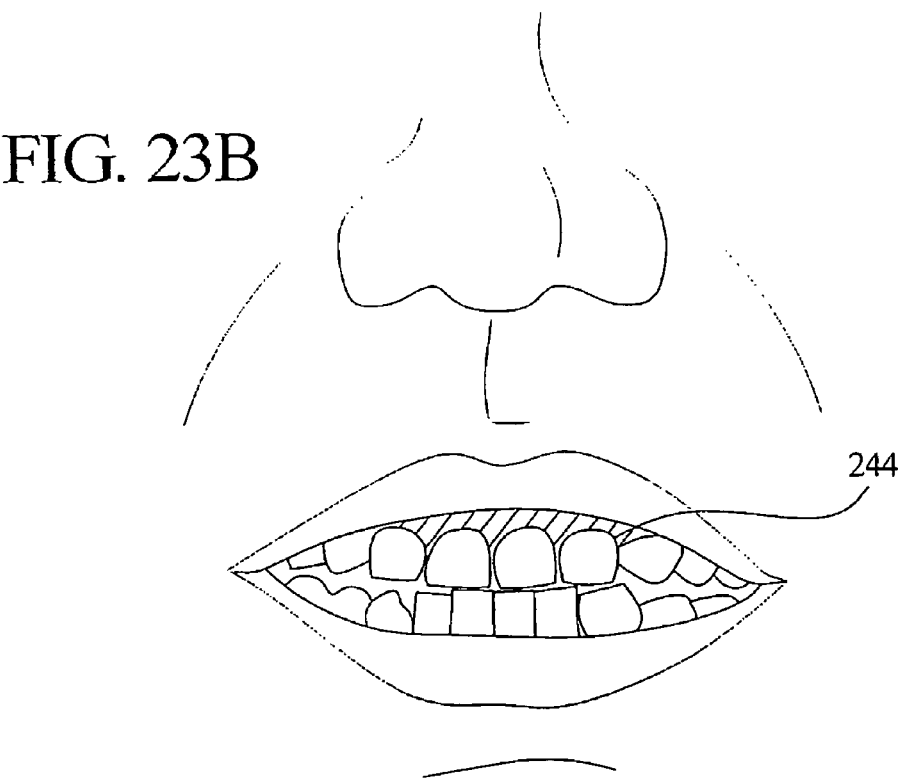
FIG. 23B illustrates a front plan view of a mouth of a patient.

Referring again to FIG. 8, the dental appliance 80 may have an increased thickness 90 at a front of the dental appliance. The dental appliance 80 may have a decreased thickness 92 at a rear end of the dental appliance. The dental appliance may then prevent an overbite 100, such as that illustrated in FIG. 9A, from developing when the permanent incisors and canines erupt into a mouth. The increased material may prevent overeruption of teeth. Moreover, the dental appliance may prevent an excessive amount of gum tissue 242 from being exposed, as illustrated in FIG. 23A. After the teeth have been prevented from erupting into an overbite 100, a reduction occurs in an amount of gum tissue 244 that may be exposed by the patient, as illustrated in FIG. 23B.

Figure 24:
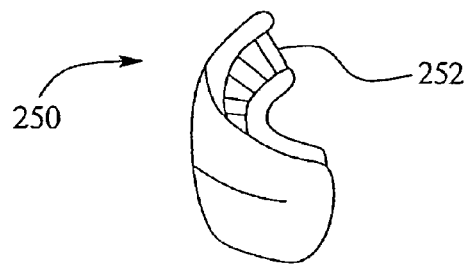
FIG. 24 illustrates a side perspective view of a dental appliance in an embodiment of the present invention.

FIG. 24 illustrates a dental appliance 250 which may fit a portion of a dentition of a patient. For example, the dental appliance 250 may be worn in only a front portion of the mouth of the patient. A rear portion 252 of the dental appliance 250 may not contact the rear teeth of the patient. In alternate embodiments, the dental appliance 250 may have only preformed and/or customized sockets, a single slotted preformed dental appliance or a combination of both prefabricated and/or customized socket and prefabricated slotted appliance.

Figure 25A:
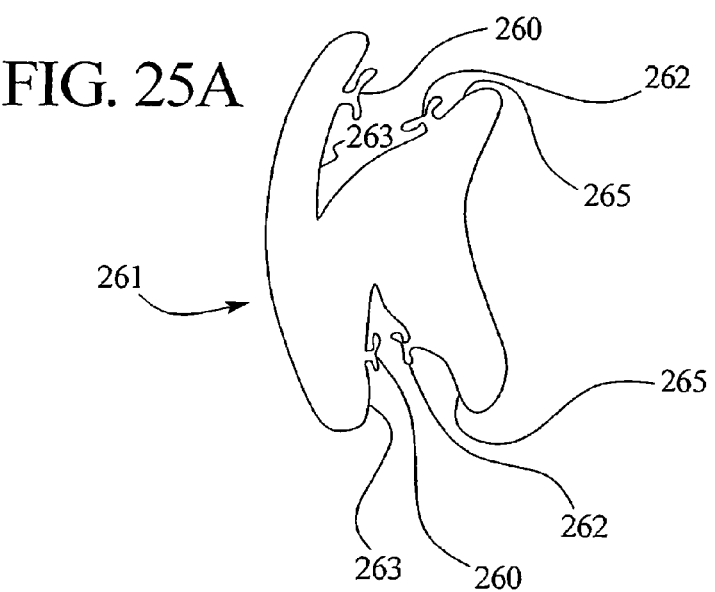
FIG. 25A illustrates a cross-sectional view of a dental appliance in an embodiment of the present invention.
Figure 25B:
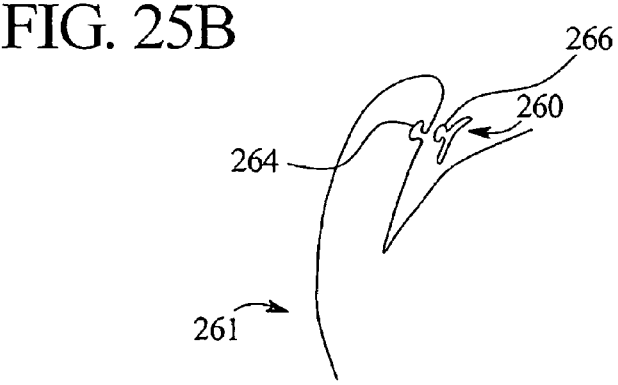
FIG. 25B illustrates a partial cross-sectional view of a dental appliance in an embodiment of the present invention.

In an embodiment, as illustrated in FIG. 25A, a dental appliance 261 may have suction cups 260 molded on a labial side 263 and/or buccal surface (not shown). Suction cups 262 may be located on a lingual side 265 of the anterior area or posterior area (not shown). The suction cups 260, 262 may engage the teeth and may move the teeth into a proper position. The suction cups 260, 262 may be molded into the dental appliance 261. In an alternate embodiment, the suction cups 260 may be inserted and/or affixed to the dental appliance 261 by, for example, a mechanism utilizing a ball 266 and a socket 264.

Figure 26:
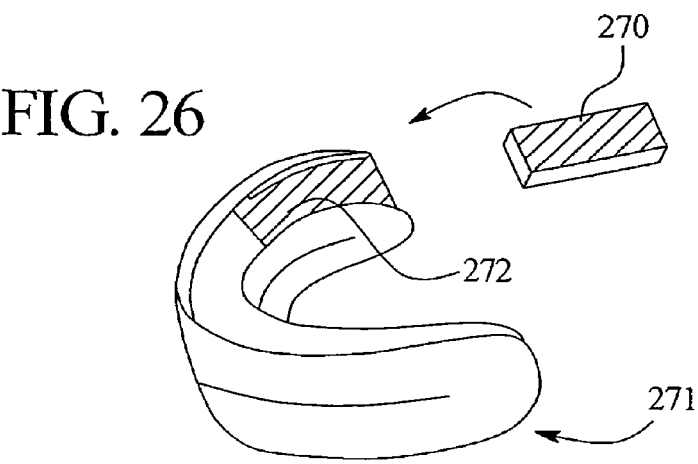
FIG. 26 illustrates a side perspective view of a dental appliance in an embodiment of the present invention.

FIG. 26 illustrates a dental appliance 271 which may receive a segment 270 of an elastomeric material. The segment 270 may be, for example, glued or otherwise attached, to a slot area 272 of the dental appliance 271. The segment 270 may place pressure against areas of the teeth to cause movement. The segment 270 may assist in correcting an open bite when placed in the posterior slot 272, or may correct overbite when placed in the anterior area.

In an embodiment, a dental appliance may be designed by a computer from digital images from photos, videos, x-rays or any other digital source or from digitized models of the mouth of the patient. The dental appliance may be formed by pressure or a vacuum onto a stereolithography created model. In an alternate embodiment, the dental appliance may be formed via stereolithography to mold the dental appliance from a three-dimensional computer generated image of a model (not shown). In an embodiment, a dental appliance may have only an upper portion which may receive upper teeth of the patient. In another embodiment, a dental appliance may have only a lower portion to receive only lower teeth of the patient. In a further embodiment, the dental appliance may straighten teeth with no adjustments or appointments wherein no subsequent orthodontics may be required. The dental appliance may be distributed over-the-counter.

In an embodiment, a larger preformed and/or enlarged customized dental appliance may be placed in the mouth of the patient to enlarge an arch for a patient having a crowding, or a potential crowding, related problem. In an embodiment, dental appliances (not shown) of graduated sizes may be used to either enlarge or reduce the size of the arch in a younger patient or an older patient. A smaller preformed and/or customized dental appliance may be placed in the mouth of the patient to constrict the arch to correct spacing or potentially spaced dentitions.

In another embodiment a fluoride and/or whitening gel may be inserted into a dental appliance. When the patient wears the dental appliance, only the teeth may touch the gel. As a result, the gel may not come in contact with the cheeks of the patient. Moreover, the dental appliance may be in close contact with the teeth wherein a minimum amount of gel may be required to treat the patient.

Figure 27:
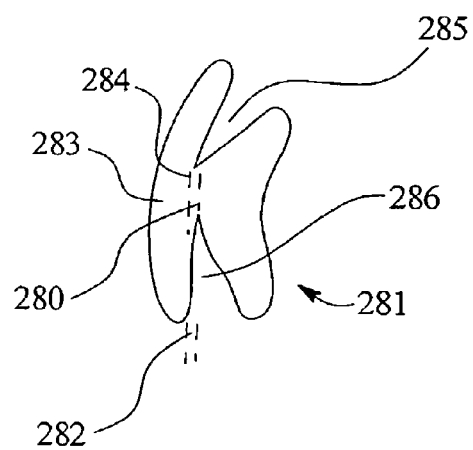
FIG. 27 illustrates a cross-sectional view of a front portion of a dental appliance in an embodiment of the present invention.
Figure 28A:
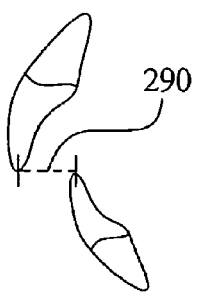
FIG. 28A illustrates a side view of an upper incisor and a lower incisor of an individual.
Figure 28B:
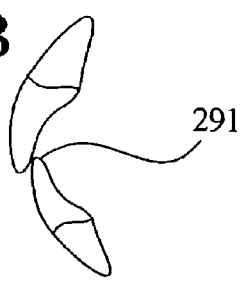
FIG. 28B illustrates a side view of an upper incisor and a lower incisor of an individual.

Referring again to FIG. 8, a cross-section of a dental appliance 80 is provided which may correct temporomandibular (TMJ) problems. The dental appliance 80 may have a greater thickness 90 at a front portion than the thickness 92 at the rear portion. In general, the antero-posterior relation between the jaws from front to back is arranged in an almost end-to-end position. FIG. 27 illustrates an almost end-to-end position where the position of an upper incisor 285 is represented vertically by line 284, and a lower incisor 286 is represented by a line 280 where the difference between the line 280 and the line 284 is almost an end-to-end relation when there is almost a zero distance at 282. The same almost end-to-end relation 282, also enables the overjet 290, illustrated in FIG. 28A, to be corrected and/or the jaws to be more ideally related front to back, as illustrated by a relation 291 in FIG. 28B.

In an embodiment, a dental appliance may have areas having different grades of material hardness, softness and/or resiliency. As a result, the dental appliance may place pressure on teeth more forcibly than known dental appliances where a harder material is utilized. The dental appliance may rotate teeth more efficiently than known dental appliances in an area in which a softer material is utilized. Buccal margins and lingual margins may also be constructed from a softer material to provide comfort to the patient. In an embodiment, the buccal margins and/or lingual margins may be constructed from a harder material to provide more movement of teeth. The dental appliance, when made of softer material, may then be less prone to cutting into gum tissue and may not cause irritation and/or sore spots.

Figure 29:
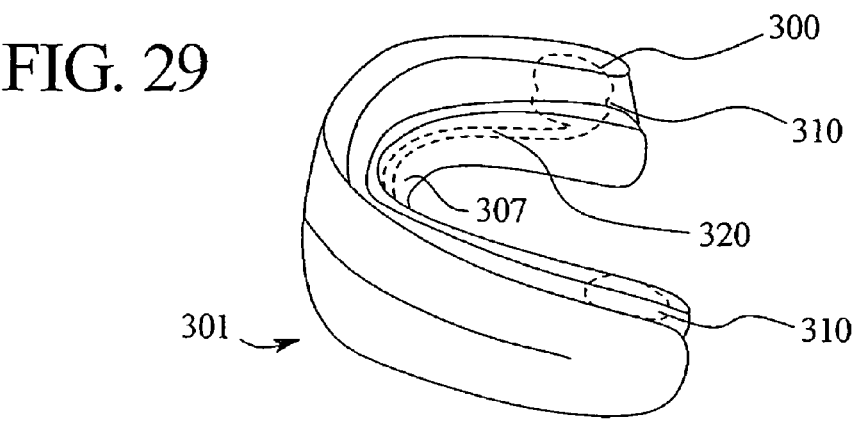
FIG. 29 illustrates a side perspective view of a dental appliance in an embodiment of the present invention.

FIG. 29 illustrates a dental appliance 301 which may combine a prefabricated-type and/or customized dental appliance with a quad-helix-type dental appliance. The resultant dental appliance 301 may have a wire 320 which may be positioned adjacent to a buccal side 300 and/or a lingual posterior side 310 and/or a lingual anterior side 307. The wire 320 may clasp onto the teeth. The wire 320 may be expanded or constricted to either expand or constrict an arch of the dental appliance 301.

Figure 30A:
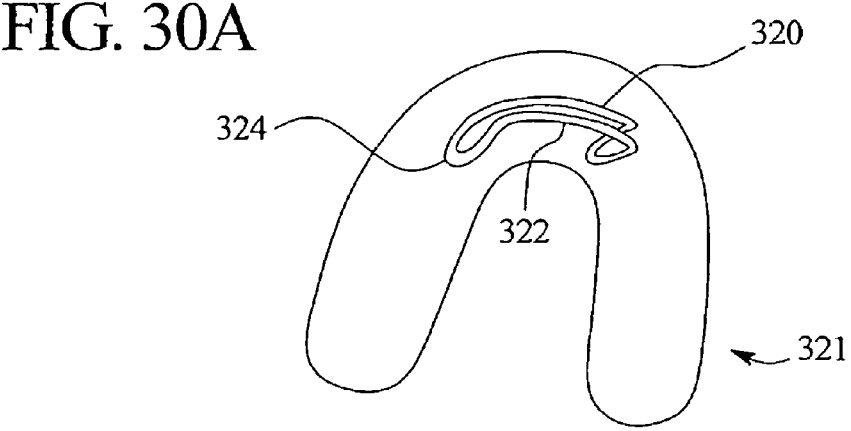
FIG. 30A illustrates a top plan view of a dental appliance in an embodiment of the present invention.
Figure 30B:
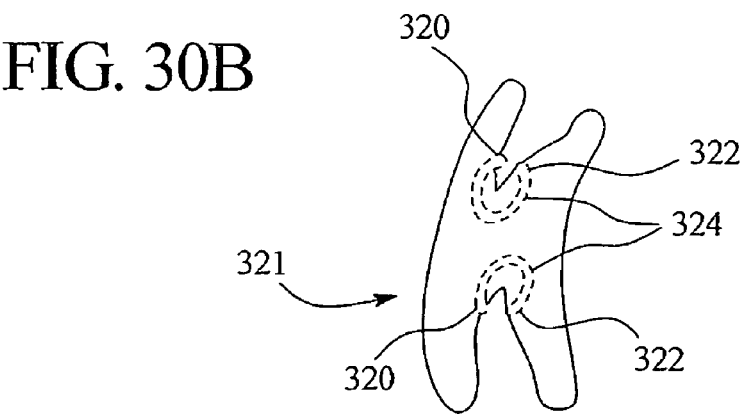
FIG. 30B illustrates a cross-sectional view of a front portion of the dental appliance of FIG. 30A.

In an embodiment, a dental appliance 321, illustrated in FIG. 30A may have a tooth aligner constructed from, for example, a wire that places a force in a lingual direction and/or a labial direction simultaneously by squeezing the front teeth to straighten them. The wire 320 may be incorporated into the dental appliance 321. The wire tooth aligner 320, 322 and 324 may assist in treating and/or straightening the incisors. FIG. 30B illustrates a cross-sectional view of the dental appliance 321. A wire 320 on a labial side may be used to put pressure lingually on the teeth. A wire 322 on a lingual side may put pressure labially on the teeth. The wire may be connected by a loop 324 that may be positioned within the dental appliance 321.

Figure 31A:
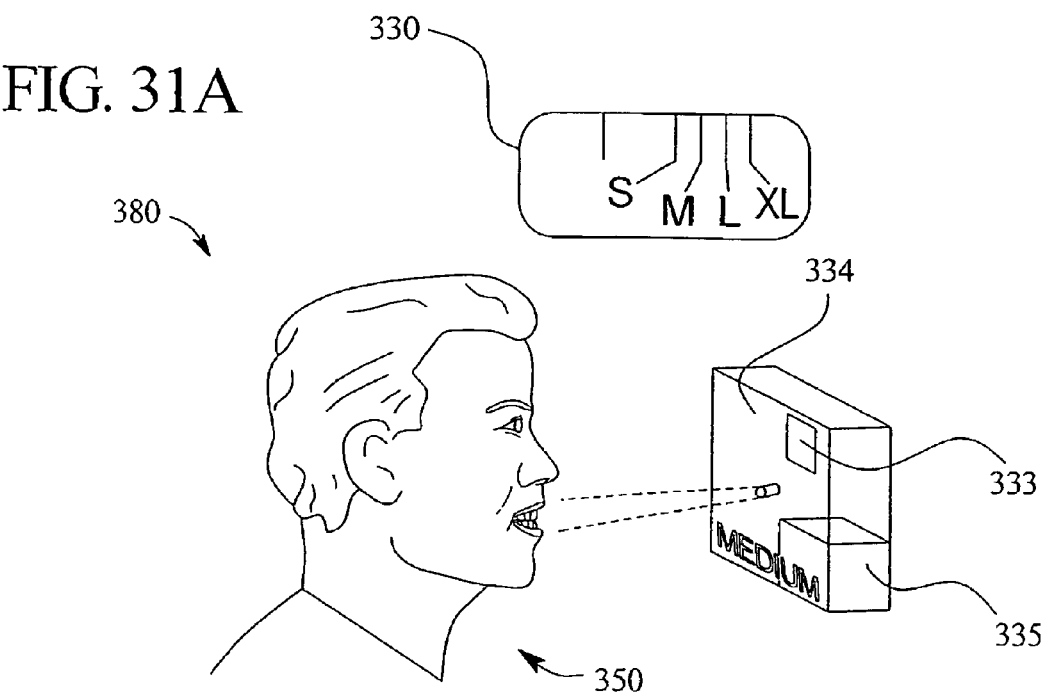
FIG. 31A illustrates a system in which a prospective patient may select a dental appliance in an embodiment of the present invention.
Figure 31B:
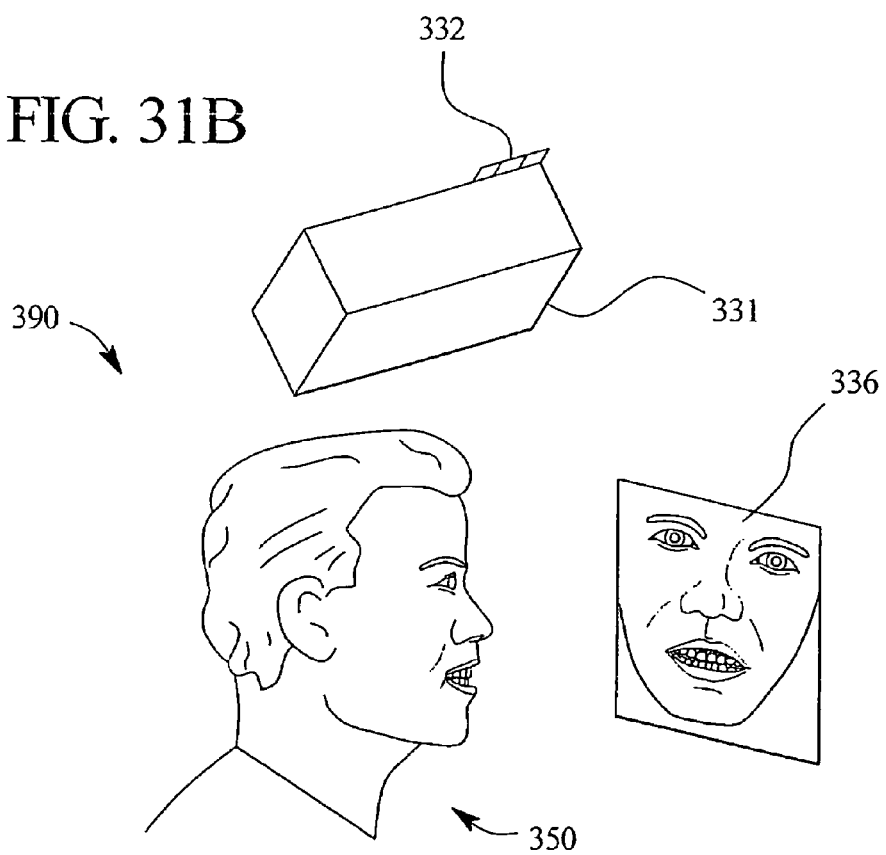
FIG. 31B illustrates a system in which a prospective patient may select a dental appliance in an embodiment of the present invention.

FIGS. 31A and 31B illustrate systems 380, 390, respectively, in which a prospective patient 350 may use various devices to select an appropriately sized dental appliance of the present invention. The patient 350 may measure one or more teeth by any method to calculate a mesio-distal width of one or more teeth. In one embodiment, the patient 350 may use a ruler 330 which may be held against a front tooth and/or teeth. In another embodiment, the dental appliance may have packaging 331 which provides an image 332 of teeth drawn to scale with which the patient 350 may compare. In an embodiment, a laser or video camera 334 having a printed display on a screen 333 and connected to an internal processor 335 may be implemented to determine a proper size of a dental appliance. In another embodiment, a single self-focusing mirror 336, such as, for example, a fresnel mirror and/or a self-focusing device as used in cameras, may be implemented by the patient 350 to determine a proper size.

In an embodiment, a patient may bite into a wax wafer and forward the wafer to a diagnosis center where a diagnosis may be provided to determine what type and/or size of dental appliance may be appropriate. The dental appliance may be delivered to the patient along with directions for use.

In an embodiment, examples of appropriate and inappropriate malocclusions to be corrected or not corrected by a dental appliance may be displayed on packaging, display posters, TV, direct mail, internet advertisements or other like methods.

In an embodiment, a video camera, digital camera, digital x-ray, or other source, may be used to take images of the dentition of the patient. A patient may turn his or her head from a first side to a second side and/or tilt his or her head upward and/or downward. The images taken of the patient may be used to provide a diagnosis. The diagnosis may be provided by a computer or by an individual and either the computer or the individual may recommend a proper type and size of a dental appliance for the patient. The dental appliance may be provided to the patient along with directions for use.

In an embodiment, the teeth of the patient may be in perfect coordination according to statistical averages as well as Bolton discrepancy standards which consists of each tooth being in a complete dentition to be perfectly coordinated with every other tooth in the same mouth and arranged in such a manner as to have a perfect occlusion, as illustrated in FIG. 5. Such a perfect coordination may enable all of the teeth of an individual with a perfectly proportioned dentition to bite into a dental appliance with all the teeth fitting into all sockets without any variations in tooth sizes. When a variation to size or arrangement is present, straightening of the variation occurs. This perfect coordination may also increase the efficiency of tooth movement and/or increase comfort for the patient when the dental appliance is worn.

It should be understood that various changes and modifications to the presently preferred embodiments described herein will be apparent to those skilled in the art. Such changes and modifications may be made without departing from the spirit and scope of the present invention and without diminishing its attendant advantages.

I claim:

1. A dental appliance adapted to be worn in a mouth of a user having one or more types of teeth, the dental appliance comprising:
    a generally U-shaped base having a flat occlusal surface wherein the flat occlusal surface is shaped to contact the teeth wherein the base is preformed and has a length defined between a first end and a second end;
    a first wall extending from the flat surface wherein the first wall defines an interior surface;
    a second wall extending from the flat surface wherein the second wall defines an exterior surface;
    a wire embedded within the base wherein one of the teeth has a first side and a second side wherein the second side is positioned opposite to the first side wherein the wire extends vertically from the base adjacent to the first side of the tooth and does not extend from the base adjacent to the second side of the tooth; and
    a slot in the base wherein the slot is defined between the first wall and the second wall wherein the slot extends along the length of the base from the first end of the base to the second end of the base wherein the slot defines a width of the flat occlusal surface wherein the width of the slot increases from a first portion of the slot to a second portion of the slot wherein the first portion of the slot is shaped to contact a front of the mouth wherein the second portion of the slot is shaped to extend rearward in the mouth and further wherein the second portion of the slot is sized to receive canine type of teeth of the user wherein the second portion of the slot is shaped to move the canine type of teeth when the base is worn by the user wherein the second portion of the slot is shaped to correct the malocclusion of the canine type teeth.

2. The dental appliance of claim 1 wherein the first portion is sized to receive an incisor type of tooth.

3. The dental appliance of claim 1 wherein the first portion of the slot is sized to receive teeth which are located toward a front of the mouth with respect to the canine type teeth of the user.

4. The dental appliance of claim 1 further comprising:
    lingual tabs formed within the interior surface wherein the lingual tabs are positioned to extend rearward into the mouth of the user when the base is worn by the user.

5. The dental appliance of claim 1 wherein the embedded wire extends from the second wall.

6. The dental appliance of claim 1 wherein the base is constructed from a first material and a second material wherein the first material is softer than the second material wherein the second portion of the slot is constructed from the first material and the first portion of the slot is constructed from the second material.

7. The dental appliance of claim 1 wherein the embedded wire extends from the first wall.

8. A method for correcting a dentition in a mouth of a user having teeth, the method comprising the steps of:
    a generally U-shaped base;
    sockets within the base wherein at least one of the sockets is preformed wherein at least one of the sockets has peripheral walls defining an interior wherein the interior is shaped to receive a first tooth wherein the peripheral walls separate a first tooth from a second tooth wherein the sockets are shaped to treat a malocclusion; and
    applying pressure to one side of the first tooth with a wire embedded within the base wherein the wire extends vertically from the base and contacts the first tooth only on the one side of the first tooth.

9. The method of claim 8 further comprising the step of:
    attaching a suction cup to the base.

10. The method of claim 8 wherein the sockets are preformed.

11. The method of claim 8 further comprising the step of:
    customizing at least one of the sockets.

12. The method of claim 8 wherein the one side of the first tooth is a lingual side that is adjacent to a tongue of the user.

13. The method of claim 8 wherein the one side of the first tooth is a labio-buccal side that is adjacent to lips of the user.

14. The method of claim 8 further comprising the step of:
    attaching a liner to the base wherein the liner has a surface which is shaped to contact the mouth to prevent the base from moving within the mouth when the base is worn by the user.

15. A dental appliance adapted to be worn in a mouth of a user having teeth, the dental appliance comprising:
    a generally U-shaped base having an occlusal surface wherein the occlusal surface contacts the teeth when the dental appliance is worn by the user;
    a first wall extending from the occlusal surface wherein the first wall defines an interior surface;
    a second wall extending from the occlusal surface wherein the second wall defines an exterior surface and wherein the first wall and the second wall define a width of the occlusal surface;
    a liquid within the generally U-shaped base wherein the liquid is released from the generally U-shaped base; and
    a wire embedded within the base wherein the wire extends vertically from a top surface of the second wall toward the teeth when the base is worn by the user wherein the wire is shaped to contact a labial side of a first tooth wherein the first tooth is an incisor type tooth.

16. The dental appliance of claim 15 further comprising:
a first socket within the occlusal surface having a first size; and
a second socket within the occlusal surface having a second size wherein the first size and the second size are different.

17. The dental appliance of claim 15 further comprising:
a labial shield extending from the second wall wherein the labial shield is shaped to cover the teeth.

18. The dental appliance of claim 15 further comprising:
lingual tabs extending from the first wall wherein the lingual tabs extend into the mouth when the dental appliance is worn by the user.

19. The dental appliance of claim 15 wherein the liquid has fluoride.

20. The dental appliance of claim 15 further comprising:
suction cups extending from the occlusal surface.

21. The dental appliance of claim 15 further comprising:
a reline material on the occlusal surface.

22. The dental appliance of claim 15 wherein the base is constructed from a first material and a second material wherein the first material is softer than the second material wherein a portion of the base that contacts the first tooth is constructed from the first material and a portion of the base that does not contact the first tooth is constructed from the second material.

23. The dental appliance of claim 15 further comprising:
a vertical slit on the exterior surface.

24. A dental appliance adapted to be worn in a mouth of a user having one or more types of teeth, the dental appliance comprising:
a generally U-shaped base having a flat occlusal surface wherein the occlusal surface is shaped to contact the teeth;
at least one socket within the occlusal surface wherein each socket has a first wall and a second wall wherein the second wall separates a first tooth from a second tooth wherein the socket is sized based on anatomical standards for teeth wherein at least one socket is shaped to receive canine type teeth regardless of anatomical variations of the canine type teeth of the user; and
a wire embedded within the base wherein the wire is shaped to contact only a labial side of one of the teeth.

25. The dental appliance of claim 24 wherein the socket is sized to receive two or more teeth.

26. The dental appliance of claim 24 wherein the socket is sized to receive one tooth.

27. The dental appliance of claim 24 further comprising:
lingual tabs extending from the base wherein the lingual tabs extend rearward into the mouth when the base is worn by the user.

28. The dental appliance of claim 24 wherein the flat occlusal surface is sized to receive two or more teeth.

29. The dental appliance of claim 24 further comprising:
fluoride within the generally U-shaped base.

30. The dental appliance of claim 24 further comprising:
a liner on the base wherein the liner is adapted to cause adhesion between the base and the teeth.

31. The dental appliance of claim 24 further comprising:
a labial shield extending from the second wall wherein the labial shield is shaped to cover the teeth.

32. A dental appliance adapted to be worn in a mouth of a user having teeth wherein a first tooth is a canine tooth, the dental appliance comprising:
a generally U-shaped base having an occlusal surface which is shaped to contact the teeth when the base is worn by the user wherein the occlusal surface has a first area wherein the first area is sized to receive the canine tooth wherein the first area is shaped to receive the canine teeth regardless of anatomical variations of canine type teeth of the user wherein the generally U-shaped base has an exterior surface;
an incisal edge within the first area of the occlusal surface wherein the incisal edge inclines outward with respect to the occlusal surface and wherein the incisal edge is sized to contact the canine tooth and further wherein the incisal edge is shaped to move the canine tooth wherein the incisal edge is shaped to prevent a malocclusion of the teeth of the user wherein a first portion of the device is constructed from a first material and contacts a first set of teeth and a second portion of the device is constructed from a second material that is softer than the first material and contacts a second set of teeth wherein the second portion of the device has the incisal edge wherein the first set of teeth and the second set of teeth are different sets of teeth; and
a wire embedded within the base wherein the wire extends vertically from the exterior surface of the generally U-shaped base toward a tooth when the base is worn by the user wherein the wire is shaped to contact only one side of the tooth.

33. The dental appliance of claim 32 further comprising:
a second base attached to the U-shaped base wherein the second base has an occlusal surface.

34. The dental appliance of claim 32 further comprising:
one or more sockets wherein the sockets are shaped to receive a second tooth wherein the second tooth is not a canine tooth.

35. The dental appliance of claim 32 wherein the wire embedded within the base contacts a labial side of the tooth.

36. The dental appliance of claim 32 wherein the occlusal surface has a second area shaped to receive a second tooth wherein the second tooth is not a canine tooth.

37. A method for treating a malocclusion in a mouth of a user having one or more types of teeth, the method comprising the steps of:
designing a generally U-shaped base having a flat occlusal surface wherein the flat occlusal surface is shaped to contact the teeth and further wherein the base is preformed;
forming a first pre-formed socket and a second pre-formed socket within the flat occlusal surface wherein the first socket is sized to receive a canine type tooth wherein the second socket is shaped to receive at least one of the teeth which is not the canine type of teeth of the user;
separating the canine type tooth from teeth which are not the canine type of teeth wherein the first socket separates the canine type tooth from teeth which are not the canine type of teeth wherein the first socket moves the canine type tooth with respect to the teeth when the base is worn by the user; and
contacting the canine type tooth with a wire embedded in the base wherein the wire extends from the base and contacts the canine type tooth only on one side of the canine type tooth.

38. The method of claim 37 further comprising the step of:
sizing the second socket to receive two or more teeth of the user.

39. The method of claim 37 further comprising the step of:
customizing the second socket to receive at least one of the teeth which is not the canine type teeth of the user.

40. The method of claim 37 further comprising the step of:
forming lingual tabs extending from the base wherein the lingual tabs extend rearward into the mouth when the base is worn by the user.

41. The method of claim 37 further comprising the step of: extending the wire into the first socket.

42. The method of claim 37 further comprising the step of: attaching a liner to the base wherein the liner adheres the base to the teeth of the user when the dental appliance is worn by the user.

43. A dental appliance adapted to be worn in a mouth of a user having one or more types of teeth, the dental appliance comprising:
a generally U-shaped base having a flat occlusal surface wherein the flat occlusal surface is shaped to contact the teeth of the user wherein the base is preformed and designed from a digital model by a computer wherein the base is sized to correspond to the digital model wherein the digital model corresponds to the teeth of the user;
sockets within the flat occlusal surface wherein the sockets have outer surfaces wherein one of the sockets is sized to receive one or more teeth of the user wherein at least one of the sockets separates a first tooth from a second tooth wherein at least one of the sockets is sized to receive a canine type tooth and to move the canine type tooth with respect to the teeth when the base is worn by the user; and
a wire embedded in the base wherein the wire extends from the outer surface of one of the sockets wherein the wire contacts the first tooth and further wherein the wire extends from only one side of the socket.

44. The dental appliance of claim 43 wherein the base is molded from a computer program.

45. The dental appliance of claim 43 wherein the base is molded by a vacuum, a pressure type device or stereolithography.

* * * * *